United States Patent [19]
Collins et al.

[11] Patent Number: 5,235,043
[45] Date of Patent: Aug. 10, 1993

[54] PRODUCTION OF BIOLOGICALLY ACTIVE, RECOMBINANT MEMBERS OF THE NGF/BDNF FAMILY OF NEUROTROPHIC PROTEINS

[75] Inventors: Frank Collins, Boulder; Tadahiko Kohno, Louisville; Jack Lile, Boulder, all of Colo.

[73] Assignee: Synergen, Inc., Boulder, Colo.

[21] Appl. No.: 594,126

[22] Filed: Oct. 9, 1990

Related U.S. Application Data

[63] Continuation-in-part of Ser. No. 547,750, Jul. 2, 1990, and a continuation-in-part of Ser. No. 505,441, Apr. 6, 1990, abandoned.

[51] Int. Cl.$^5$ .......................... C07K 3/14; C12N 15/00
[52] U.S. Cl. ..................................... 530/399; 530/402; 530/404; 530/412; 530/417; 530/418; 530/419; 530/422; 536/23.51; 536/23.5; 435/69.1; 435/71.1; 435/172.3; 435/849; 935/13
[58] Field of Search ............... 530/399, 402, 404, 417, 530/422, 412, 418, 419; 536/27; 435/69.1, 71.1, 172.3, 849; 935/13

[56] References Cited

U.S. PATENT DOCUMENTS

| | | | |
|---|---|---|---|
| 4,511,502 | 4/1985 | Builder | 530/422 |
| 4,511,503 | 4/1985 | Olson | 530/422 |
| 4,512,922 | 4/1985 | Jones | 530/422 |
| 4,599,197 | 7/1986 | Wetzel | 530/417 |
| 4,766,205 | 9/1988 | Ghosh-Dastidar | 530/417 |
| 4,929,700 | 4/1990 | Halenbeck | 530/404 |

OTHER PUBLICATIONS

Edington, *Bio/Technology*, 10:376, Apr. 1992.

*Primary Examiner*—Michael G. Wityshyn
*Assistant Examiner*—Abdel A. Mohamed
*Attorney, Agent, or Firm*—Beaton & Swanson

[57] ABSTRACT

This invention describes processes for producing mature human members of the NGF/BDNF family of neurotrophic proteins that are fully biologically active. In addition, the gene encoding human BDNF and processes for obtaining the same are disclosed.

A previously-unreported member of the NGF/BDNF family of neurotrophic proteins, NGF-3, has been identified and a portion of the gene encoding for the NGF-3 has been described. Processes for identifying additional previously unreported members of the NGF/BDNF family are also described.

7 Claims, 11 Drawing Sheets

FIGURE 1

```
ATG ACC ATC CTT TTC CTT ACT ATG GTT ATT TCA TAC TTT GGT TGC ATG AAG GCT GCC
 M   T   I   L   F   L   T   M   V   I   S   Y   F   G   C   M   K   A   A
CCC ATG AAA GAA GCA AAC ATC CGA GGA CAA GGT GCC TTG CCA GGT GTG CGG
 P   M   K   E   A   N   I   R   G   Q   G   A   L   P   G   V   R
ACC CAT GGG ACT CTG GAG AGC GTG GAG AAT GGG CCC AAG GCA TTT GGT TCA AGA GGC TTG ACA
 T   H   G   T   L   E   S   V   E   N   G   P   K   A   F   G   S   R   G   L   T
TCA TTG GCT ACT GAC ACT TTC GAA TTC CAC GTG ATA GAG CTG TTG TAC TGC ATG CAG GTG AAA
 S   L   A   T   D   T   F   E   F   H   V   I   E   L   L   Y   C   M   Q   V   K
GTT CGG CCC AAT GAA GAA AAC AAG AAT AAG GAC GCA TTG ACG TCC AGG GTG ATG
 V   R   P   N   E   E   N   K   N   K   D   A   L   T   S   R   V   M
CTC AGT CAA GTG CCT TTG GAG ATG CCT CTT CTT TTT CTG CTG GAG GAA TAC AAA
 L   S   Q   V   P   L   E   M   P   L   L   F   L   L   E   E   Y   K
AAT TAC CTA GAT GCT GCA AAC ATG TCC ATG AGT CCG AGG ATT CGG CAC GTC TCT GAC CCT GCC
 N   Y   L   D   A   A   N   M   S   M   S   R   R   I   R   H   V   S   D   P   A
CGC CGA GGG GAG CTG GTG AGC ATG TGT GAC GGG AGT ATT TGG GTA GAG ACG GCA GAC
 R   R   G   E   L   V   S   M   C   D   G   S   I   W   V   E   T   A   D
AAA AAG ACT GCA GTG GAC ATG AAG GGG ACG GGG TAC TAC ACA GTC CTT GAA AAG CCT
 K   K   T   A   V   D   M   K   G   T   G   Y   Y   T   V   L   E   K   P
GTA TCA AAA GGC CAA CTG AAG TAC TTC TAC AAA AAG TGC AAT TCC AGA ATG GGT
 V   S   K   G   Q   L   K   Y   F   Y   K   K   C   N   S   R   M   G
TAC ACA GAA GAA TGC AGG GGC CAA GGC ATA GAC AAG ATG CAT CAT AAC TCC CAG TGC CGA
 Y   T   E   E   C   R   G   Q   G   I   D   K   M   H   H   N   S   Q   C   R
ACT ACC CAG TCG TAC TAC GTG CGG CTT ACC ATG AGC AGC AAG TGG TGG TGG
 T   T   Q   S   Y   Y   V   R   L   T   M   S   S   K   W   W   W
CGA TTC ATA AGG ATA GAC GAC TGT GTA ACT TGT AAA AGG AGA AGA GGA AGA
 R   F   I   R   I   D   D   C   V   T   C   K   R   R   R   G   R
TAG
stop
```

FIGURE 6

```
bdnf   ATG      CATCCTTTCCTTACTATGGTTATTTCATACTTTGGTTGCATGAAGGCTGCCCCATGAAAGA
ngf-3  ATGTCCATCTTGTTTATGTGATATTTCTCGCTTATCTCCGTGGCATCCAAGGTAACAACATGATCA
ngf    ATGTCCATGTTGTGTTCTACACTCTGATCACAGCTTTTCTGATCGGCATACAGGCGAACCACACTCAGA AGCAAACATCCGAGGACAAGGT------GGCTTGGCCTACCCAGGTGCGG---ACC------CATGGGACTCT
AAGGAGTTTGCCAGAAGACTCGCTCATTCCCTCATTATTAAGCTGATCCAGGCAGATATTTGAAAAACAAGCT
GAGCAATGTCCCTGCA---GGA------ACCATCCCCCAAGTCCACTGGACTAAACTTCAGCATTCCCT GGAGAGC-------GTGAATGGGCCCAAGGCAGGTTCAAGAGGCTTGACATCATTGGCTGACACTTTCGAACACGT
CTCCAAGCAGATGGTGGACGTTAAGGAAAATTACCAGAGACCACCCTGCCCAAAGCTGAGGCTCCCCGAGAGCCGGA
TGAC------ACTGCC---CTTCGCAGAGCC---CGCAGCGCC---CCG---GCAGCGGCGATAGCTGCACGCGT GATAGAGAGCTGTGTTGGATGATGAGGAC----CAGAAAGTTCGGCCCAATGAAGAAAAC--------AATAAGGACGCAGA
GCGGGGAGGGCCCCGCCAAGTCAGCATTCCAGCCAAGTGATTGCAATGGACACCGAACTGCTGCGACAACAGAGACG
GGCGGGG---CAGACCCGC---AACATT---ACTGTG--------GACCCCAGGCTGTTT---AAAAAGCGGCG CTTGTACACGTCCAGGTGATGCTCAGTAGTCAAGTGCCTTTGGAGCCTCCTCTTCTTCTTCTGCTGAGGAATA
CTACAACTCACCGGGTCCTGGGTCCTGAGCGACACACCCCCTTGGAGCCCCCCGTGTATCTCATGGAGGATTA
ACTCCGTTCACCCCGTGTGCTGTGTTTAGCACCCCAGCCTCCCCGTGAAGCTGCAGACACTCAGGATCTGGACTTCGA CAAAATTACCTAGATGCTGCAAACATGTCCAAACATGTCCATGAGGGTCCGGCGC------CACTCTGACCCTGCCCGCCGAGG
CGTGGGCAGCCCGTGGCCGAACAGAACATCACGGGCGGAAACGG---TACGGGAGCATAAGAGTCACCGAGG
GGTCGGTGGTGCTGCCCCCTTCAACAGAGACTCACAGGAGCAAGCGGTCATCATCCCATCTTCCACAGGGG GGAGCTGAGCGTGTGTGACAGTATTAGTGAGTGGGTAACGGCGGCAGACAAAAGACTCAGTGGACATGTCGGG
GGAGTACTCGGTATGTGACAGTGAGAGTCTGTGGGTGACC----GACAAGTCATCGGCCATCGACATTCGGGG
CGAATTCTCGGTGTGGTGACAGTGCAGCGTGTCAGCGTGTGGG----GATAAGACCGCCACAGACATCAAGGG CGGGACGCGTCACAGTCCTTGAAAAGGTCCCTGTATCAAAAGGCCAACTGAAGCAATACTTCTACGAGACCAAGTG
ACACCAGGTCACGGTGCTCGGGTATGTGACAGTGCAACTCTCCGTCAAACAATATTTTATGAAACGCGATG
CAAGGAGGTGATGGTGTTGGGAGAGGTGAACATTAACAACAGTGTATTCAAACAGTACTTTTTTGAGACCAAGTG
```

FIGURE 6 (continued)

```
CAATCCCATGGTTACACAAAAGAAGGCTGCAGGGCATAGACAAAAGGCATTGGAACTCCCAGTGCCGAACTAC    bdnf
TAAGGAAGCCAGGCCGGTCAAAAACGTTGCAGGGTATTGATGATAAACACTGGAACTCTCAGTGCAAAACATC    ngf-3
CCGGGACCCAAATCCCGTTGACAGCGGGTGCCGGGGCATTGACTGAACTCAAAGCACTGGAACTCATATTGTACCACGAC  ngf CCAGTCGTACGTGCGGGCCCCTTACCATGGATAGCAGAAAGAGAATTGGCTGCGATTCATAAGGATAGACACTTC    bdnf
CCAAACCTACGTCCGAGCACTCGACTTCAGAGAACAATAAACTCGTGGGCTGGGCGTGGATACGGATAGACACGTC    ngf-3
TCACACCTTTGTCAAGGCGCTGACCATGATGGC---AAGCAGGCTGCCTGGCGGTTTATCCGGATAGATACGGC    ngf TTGTGTATGTACATTGACCATTAAAAGGGGAAGATAG                                         bdnf
CTGTGTGTGTGTGCCTTGTCGAGAAAAATCGAAGAACATGA                                     ngf-3
CTGTGTGTGTGTGCTCAGCAGGAAGGCTGTGAGAAGAGCCTGA                                   ngf
```

FIGURE 7

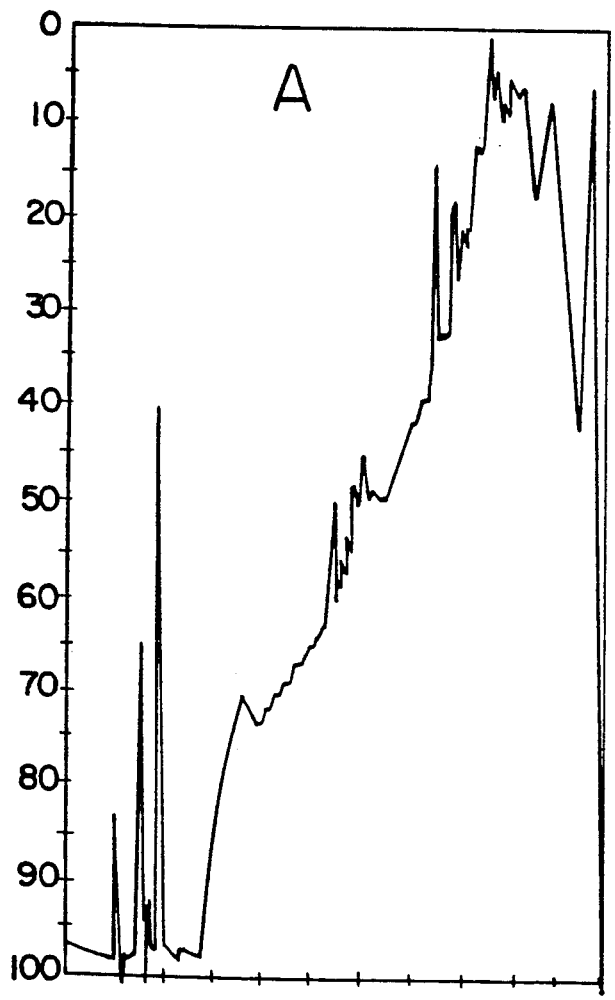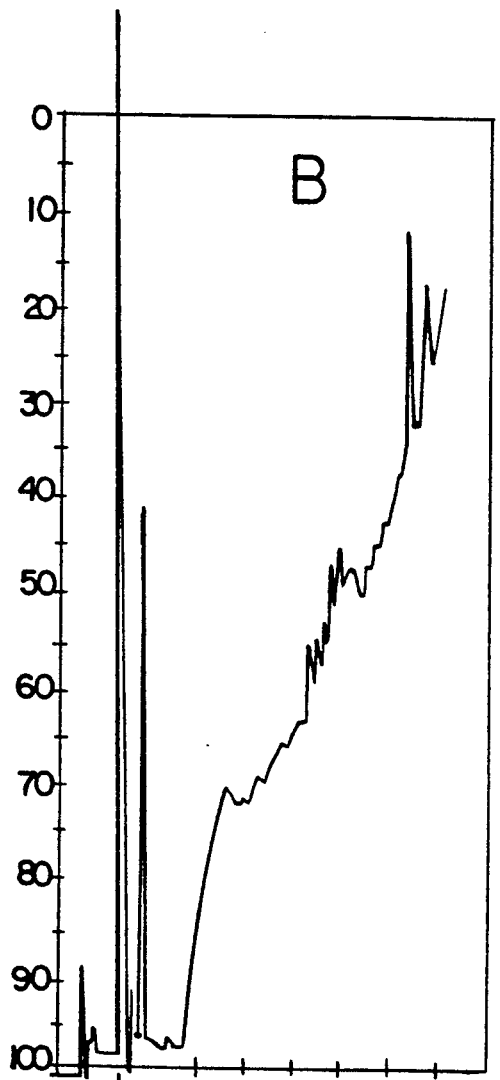
SAMPLE = 50 μl FINAL REFOLDING MIXTURE + 100 ng NATIVE NGF
FIG.11A
SAMPLE = 50 μl FINAL REFOLDING MIXTURE
FIG.11B

PRODUCTION OF BIOLOGICALLY ACTIVE, RECOMBINANT MEMBERS OF THE NGF/BDNF FAMILY OF NEUROTROPHIC PROTEINS

CROSS-REFERENCE TO RELATED APPLICATIONS

This is a continuation-in-part of co-pending application Ser. No. 07/547,750 filed Jul 2, 1990 pending and Ser. No. 07/505,441 filed Apr. 6, 1990, now abandoned for "Production of Biologically Active, Recombinant Members of the NGF/BDNF Family of Neurotrophic Proteins."

FIELD OF THE INVENTION

This invention relates to processes for the production of recombinant members of the human NGF/BDNF family of neurotrophic proteins in biologically active forms. In addition, this invention discloses processes for identifying previously unreported members of this family of proteins and the subsequent production of these proteins.

BACKGROUND OF THE INVENTION

Neurotrophic factors are natural proteins, found in the nervous system or in non-nerve tissues innervated by the nervous system, whose function is to promote the survival and maintain the phenotypic differentiation of nerve and/or glial cells (Varon and Bunge 1978 Ann. Rev. Neuroscience 1:327; Thoenen and Edgar 1985 Science 229:238). Because of this physiological role, neurotrophic factors may be useful in treating the degeneration of nerve cells and loss of differentiated function that occurs in a variety of neurodegenerative diseases, such as Alzheimer's or Parkinson's diseases, or after traumatic injuries, such as stroke or physical trauma to the spinal cord (Appel 1981 Ann. Neurology 10:499).

In order for a particular neurotrophic factor to be potentially useful in treating nerve damage, the class or classes of damaged nerve cells must be responsive to the factor. Different neurotrophic factors typically affect distinctly different classes of nerve cells. Therefore, it is advisable to have on hand a variety of different neurotrophic factors to treat each of the classes of damaged neurons that may occur with different forms of disease or injury. A given neurotrophic factor, in addition to having the correct neuronal specificity, must be available in sufficient quantity to be used as a pharmaceutical treatment. Also, since neurotrophic factors are proteins, it would be desirable to administer to human patients only the human form of the protein, to avoid an immunological response to a foreign protein.

Since neurotrophic factors are typically present in vanishingly small amounts in tissues (e.g., Hofer and Barde 1988 Nature 331:261; Lin et al. 1989 Science 246:1023) and since human tissues are not readily available for extraction, it would be inconvenient to prepare pharmaceutical quantities of human neurotrophic factors directly from human tissues. As an alternative, it would be desirable to isolate the human gene for a neurotrophic factor and use that gene as the basis for establishing a recombinant expression system to produce potentially unlimited amounts of the human protein.

Two neurotrophic factors have been described that are closely related in amino acid sequence but which affect different, although partially overlapping, sets of responsive neurons (Leibrock et al. 1989 Nature 341:149). These two neurotrophic factors are: (1) nerve growth factor (NGF) and (2) brain-derived neurotrophic factor (BDNF). Both NGF and BDNF are apparently synthesized as larger precursor forms which are then processed, by proteolytic cleavages, to produce the mature neurotrophic factor (Edwards et al, 1986 Nature 319:784; Leibrock et al. 1989 ibid.). The only genes for members of the proposed NGF/BDNF family of neurotrophic proteins that have been reported to date are the human and various animal genes for NGF (Scott et al. 1983 Nature 302:538; Ullrich et al. 1983 Nature 303:821; Meier et al. 1986 EMBO J. 5:1489) and the pig gene for BDNF (Leibrock et al. 1989 ibid.). There is a significant similarity in amino acid sequences between mature NGFs and mature BDNF, including the relative position of all six cysteine amino acid residues, which is identical in mature NGFs and BDNF from all species examined (Leibrock et al 1989 ibid.). This suggests that the three-dimensional structure of these two proteins, as determined by the location of disulfide bonds, is similar. Both mature proteins also share a basic isoelectric point (pI). NGF and BDNF are neurotrophic factors for different, although partially overlapping, sets of responsive neurons.

Therefore, NGF and BDNF appear to define a family of structurally related neurotrophic proteins which are likely to differ in their physiological role in the organism, each member affecting a different set of responsive neurons. It would be desirable to isolate the genes for any and all additional members of this NGF/BDNF family, in order to have a battery of neurotrophic proteins available to treat the range of different nerve cell types whose functions are compromised in various forms of damage to the nervous system.

NGF is a neurotrophic factor for cholinergic neurons in the basal forebrain, among others (Hefti and Will 1987 J. Neural Transm. [Suppl] (AUSTRIA) 24:309). The functional inactivation and degeneration of the basal forebrain cholinergic neurons responsive to NGF in the course of Alzheimer's disease is thought to be the proximate cause of the cognitive and memory deficits associated with that disease (Hefti and Will 1987 ibid.). NGF has been shown to prevent the degeneration and restore the function of basal forebrain cholinergic neurons in animal models related to Alzheimer's disease, and on this basis has been proposed as a treatment to prevent the degeneration and restore the function of these neurons in Alzheimer's disease (Williams et al. 1986 Proc. Natl. Acad. Sci. USA 83:9231; Hefti 1986 J. Neuroscience 6:2155; Kromer 1987 Science 235:214; Fischer et al 1987 Nature 329:65).

BDNF is a neurotrophic factor for sensory neurons in the peripheral nervous system (Barde 1989 Neuron 2:1525). On this basis, it is possible that BDNF may prove useful for the treatment of the loss of sensation associated with damage to sensory nerve cells that occurs in various peripheral neuropathies (Schaumberg et al, 1983 "Disorders of Peripheral Nerves" F. A. Davis Co., Philadelphia, Pa.). NGF and BDNF may be shown in the future to have additional neurotrophic effects that indicate their potential usefulness in treating other kinds of nerve system damage. Also, new members of the NGF/BDNF family of neurotrophic proteins may support additional neuronal populations and, therefore, be of value in treating yet additional kinds of nerve damage.

In accordance with the principle expressed above that one should administer only human proteins to human patients, it would be desirable to obtain the human gene for BDNF in order to manufacture the human protein. Also in accordance with this principle and with the principle expressed above that it would be desirable to have a battery of neurotrophic proteins with differing neuronal specificities to treat a variety of neurological conditions, it would be desirable to obtain the human genes for any and all additional members of the NGF/BDNF family of neurotrophic proteins.

Recombinant expression systems that are capable of producing the large quantities of fully-biologically-active and structurally-unmodified mature NGF needed for pharmaceutical development and for the treatment of patients have not generally been described. See, however, European Patent Publication EP 89113709, describing the recombinant expression of NGF in insect cells. Mature NGF with these properties can be produced when human or animal NGF genes are expressed in eukaryotic cell expression systems (e.g., Edwards et al. 1988 Molec. Cell. Biol. 8:2456). In such systems, the full-length NGF precursor is first synthesized and then proteolytically processed to produce mature NGF which is correctly folded 3-dimensionally and is fully biologically active. However, eukaryotic cell expression systems in general, and specifically those reported for NGF, produce relatively low yields of NGF per gram of cells and are relatively expensive to use in manufacturing.

In contrast, expression systems that use prokaryotic cells, such as bacteria, generally yield relatively large amounts of expressed protein per gram of cells and are relatively inexpensive to use in manufacturing. However, an adequate bacterial expression system capable of producing fully-biologically-active and structurally-unmodified mature NGF has not been described (a bacterial expression system is disclosed in Canadian Patent No. 1,220,736). This failure can probably be traced to problems associated with bacterial expression systems in general and problems associated with the specific techniques employed to produce NGF in bacteria.

Bacteria are not able to correctly process precursor proteins, such as the precursor protein for NGF, by making appropriate proteolytic cleavages in order to produce the correct smaller mature protein. Therefore, to produce mature NGF in bacteria, it is necessary to express only that portion of the NGF DNA sequence encoding the mature protein and not that for the larger precursor form. When this was done in the bacterium *Escherichia coli*, relatively large amounts of the mature human NGF protein were produced (see, e.g., Iwai et al. 1986 Chem. Pharm. Bull. 34:4724; Dicou et al. 1989 J Neurosci, Res. 22:13). Unfortuntely, the bacterially-expressed protein had little or no biological activity.

The likely reason for this lack of biological activity is that the mature NGF protein was unable to assume spontaneously the correct 3-dimensional structure and form the correct intramolecular disulfide bonds, both of which are essential for biological activity. Therefore, it would appear necessary to develop a refolding protocol capable of restoring to the mature NGF produced in bacteria the 3-dimensional structure and intramolecular disulfide bonding pattern required for full biological activity.

A refolding protocol has been descried in European Patent Application 336,324 which restores some biological activity to mature NGF produced in bacteria. However, this protocol has serious deficiencies. The protocol uses exposure to high pH (pH 13 is recommended)—apparently to break disulfide bonds that may have formed incorrectly in the bacterially-produced NGF—followed by lowering of the pH—apparently to allow the opportunity for the correct intramolecular disulfide bonds to form. Exposure to high pH, as used in this protocol, is known to cause extensive modification of proteins, including the elimination of amine side chains in glutamine and asparagine (of which there are 7 in mature human NGF) and extensive chemical alteration of asparagine-glycine, asparagine-serine and asparagine-threonine adjacent pairs (of which there are 2 in mature human NGF). In addition to these chemical modifications, the refolding procedure appeared to restore only approximately one-tenth of the biological activity of NGF. The protocol described in European Patent application 336,324 would, therefore, appear to be inadequate to produce fully-biologically-active and chemically-unmodified mature human NGF. Although numerous protocols for refolding and renaturing proteins that do not involve harsh conditions exist, no such procedure has been applied successfully to NGF.

Therefore, mature human NGF has been unavailable in sufficient amounts for pharmaceutical use, due apparently to the inadequate production capacity and cost of eukaryotic expression systems and the inability of the bacterial expression systems so far described to produce biologically-active and chemically-unmodified mature NGF. Since human mature NGF is perceived as having a potential usefulness in the treatment of Alzheimer's disease, the unavailability of this material has been keenly felt by the scientific and clinical communities. The unavailability of biologically-active human mature NGF was seen by a panel of leading scientists, assembled by the National Institute on Aging, as the critical block to further development of NGF as a treatment for Alzheimer's disease (Phelps et al. 1989 Science 243:11).

It is presumed that similar manufacturing difficulties would apply to each member of the NGF/BDNF family of neurotrophic proteins, since members of this family so far described have identically located cysteine amino acid residues and presumably, therefore, form a pattern of intramolecular disulfide bonds identical to that of NGF (Angeletti et al. 1973 Biochemistry 12:100). Based on this consideration, a manufacturing system capable of producing fully-biologically-active and chemically-unmodified human mature NGF in large amounts in bacteria will be useful in producing similar large amounts of any member of the NGF/BDNF family in a biologically-active and unmodified form suitable for pharmaceutical use.

In view of the apparent value of such neurotrophic proteins and the current inability to produce biologically active proteins as indicated above, it would be desirable to provide the following: (1) methods for securing the genes for any and all additional neurotrophic proteins that are structurally related to NGF and BDNF in a manner similar to the way these two proteins are related to each other; (2) methods for obtaining the human genes for all members of the NGF/BDNF family for which this has not been done, including the human gene for BDNF; (3) methods for using the human genes to establish recombinant expression systems in microorganisms such as E. coli that will produce significant quantities of the mature (processed) form of each of these human proteins; and, (4) a procedure for refolding and renaturing the recombinant mature proteins to allow them to attain a biological specific activity, expected for members of this class of neurotrophic proteins.

SUMMARY OF THE INVENTION

The present invention relates to processes for the production of biologically active members of the NGF/BDNF family of neurotrophic proteins, to the nucleic acid sequence of the gene coding for human BDNF and the inferred amino acid sequence for human BDNF, and to the nucleic acid sequences of genes coding for previously unreported members of this family of neurotrophic proteins including NGF-3 and the inferred amino acid sequences of such proteins.

A process for identifying previously unreported members of the neurotrophic protein family is set forth and a process for expressing such identified proteins in an efficient bacterial expression system, specifically in *Escherichia coli*, is set forth. In addition, a process for restoring biological activity to mature but biologically inactive human neurotrophic proteins produced in bacteria is described.

More specifically, a system for the expression of NGF and the effective renaturing of human mature NGF in a biologically active form is described. A previously undescribed member of the NGF/BDNF family of neurotrophic proteins, designated herein as NGF-3, has been identified, and the nucleic acid sequence of the human gene coding for NGF-3 has been identified and the inferred amino acid sequence of NGF-3 described.

The present invention also includes the production of purified forms of all members of the NGF/BDNF family of neurotrophic proteins which would be valuable as pharmaceutical preparations for treating the degeneration of nerve cells and loss of differentiated function that occurs in a variety of neurodegenerative diseases.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 1 depicts the nucleic acid and inferred amino acid sequences of human BDNF. The inferred amino acid sequence of the mature (processed) form of BDNF is in bold.

FIG. 6 compares the nucleic acid sequence of NGF-3 to the sequence of NGF and BDNF. Gaps, indicated by dashes, correspond to the location of gaps used to align the amino acid sequences (see FIG. 7). The partial nucleic acid sequence of NGF-3 obtained by PCR is underlined.

FIG. 7 compares the amino acid sequence of NGF-3 to the sequence of NGF and BDNF. The inferred sequences of the mature proteins are in bold. Each amino acid underlined in the mature sequence of BDNF or NGF is identical to the corresponding amino acid in NGF-3. Each amino acid underlined in the mature sequence of NGF-3 is identical to the corresponding amino acids in both NGF and BDNF. Gaps, indicated by dashes, were placed in the sequences to increase alignment.

FIG. 11 depicts the analysis on reversed-phase high performance liquid chromatography of (A) 50 μl of the final refolding mixture assayed in FIG. 10 to which 100 ng of native, insect cell-produced NGF has been added, and (B) 50 μl of the final refolding mixture to which no native, insect cell-produced NGF has been added. The position at which native, insect cell-produced NGF normally runs on this column has been indicated by the label NGF followed by an arrow.

DESCRIPTION OF THE PREFERRED EMBODIMENTS

Figure 2:
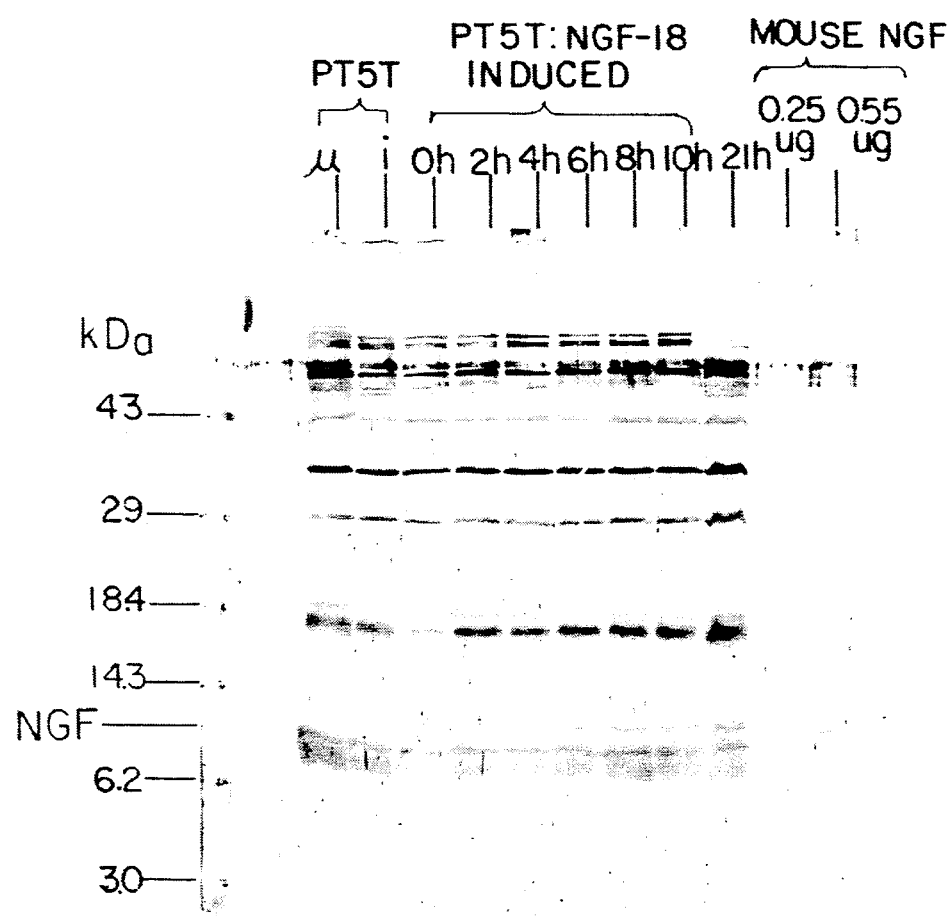
FIG. 2 depicts the expression of human mature (processed) NGF in *E. coli* in vector pT5T. The details are given in the text of Example 2.

Reference will now be made in detail to the presently preferred embodiments of the invention which, together with the following examples, serve to explain the principles of the invention.

1. Isolation of Human BDNF

In one embodiment of the present invention methods are provided for obtaining the human gene coding for the precursor and mature forms of BDNF. The present invention includes the mature and precursor forms of human BDNF, and the genes that code for such proteins. Throughout this application, the mature form of a neurotrophic protein refers to the biologically active form of the protein as it exists in nature after proteolytic cleavage. The precursor form of a neurotrophic protein refers to the protein coded for by the human gene prior to proteolytic cleavage. In a preferred version of this embodiment, and as described in Example 1 below, synthetic oligonucleotides BDNF-1, BDNF-2, BDNF-2A, BDNF-2B, BDNF-3, BDNF-4 and BDNF-5, approximately 15-30 bases in length, were prepared based on various regions of the nucleic acid sequence encoding pig BDNF. These pig BDNF oligonucleotides are used in various combinations as primers in the polymerase chain reaction (PCR) with human genomic DNA as template to amplify intervening segments of the human gene for BDNF. The amplified fragments are subcloned and the subclones screened for those that hybridize to an additional oligonucleotide probe representing sequences located between those of the two primers used in PCR.

Positive subclones isolated in this screening may be sequenced to confirm their identity as portions of the BDNF gene. One or more of these amplified fragments may be used to screen a human genomic DNA library in order to obtain the human gene for BDNF. Subcloned restriction fragments of human genomic clones may be sequenced in order to provide the nucleic acid and inferred amino acid sequences coding for the precursor and mature forms of human BDNF. The nucleic acid and inferred amino acid sequences of human BDNF, obtained according to these procedures and included within the scope of this invention, are set forth in FIG. 1.

2. Identification of Previously Undescribed Members of the NGF/BDNF Family of Neurotrophic Proteins In one embodiment of the present invention methods are provided for obtaining the human genes coding for the precursor and mature forms of previously-unreported, new members of the NGF/BDNF family of neurotrophic proteins. The desired human DNA sequences are any and all previously-unreported sequences that code for proteins which are not identical to human NGF or BDNF but are clearly related to NGF or BDNF with respect to possible defining characteristics of the family. Such characteristics may include one or more of the following: neurotrophic activity in an appropriate bioassay; significant homology in amino acid sequence including both amino acid identities and conservative substitutions; conserved location of cysteine residues in the amino acid sequence; hydrophobic signal sequences for secretion of the protein; signal sequences for proteolytic processing to a mature form; and/or basic isoelectric point of the processed protein.

A. In one preferred version of this embodiment, several synthetic oligonucleotide, approximately 15–40 bases in length, may be prepared based on a number of both conserved and variable regions of the nucleic acid sequences encoding animal and human NGFs and BDNFs. These NGF/BDNF oligonucleotide may be used in various combinations as primers in PCR with human genomic DNA or human cDNA libraries prepared from a variety of discrete regions of the nervous system as templates in order to amplify intervening segments of the human genes for members of the NGF/BDNF family.

Using cDNAs from discrete regions of the nervous system may be advantageous since (1) regions that do not contain significant amounts of the messages for NGF and BDNF may reduce the background of fragments amplified by PCR from NGF and BDNF themselves; and, (2) neurotrophic factors that affect desired neuronal populations are likely to be located in predictable regions of the nervous system.

The amplified fragments may be subcloned and individual subclones selected for sequencing either (a) by positive hybridization to a degenerate oligonucleotide representing DNA sequences located between those of the oligonucleotide primers, or (b) by restriction mapping to detect subclones containing an insert of approximately the size one would expect to be amplified from NGF or BDNF.

Such selected subclones may be sequenced to determine whether they represent portions of the gene for NGF, BDNF, or new members of the NGF/BDNF family. If the subcloned, amplified fragment appears to represent a new member of the NGF/BDNF family, this fragment may be radiolabeled and used to screen a human genomic DNA library in order to obtain the human gene for the putative new neurotrophic protein. The human gene may be sequenced in order to provide the nucleic acid and inferred amino acid sequences coding for the precursor and mature forms of the new neurotrophic protein.

B. In a second preferred version of this embodiment, subclones of the fragments amplified by PCR as described above, may be screened with each of several non-degenerate DNA fragments that are specific for the NGF or BDNF genes. The purpose of this screening is to facilitate isolation of fragments amplified from genes for new members of the NGF/BDNF family, by eliminating fragments amplified from the already characterized members NGF and BDNF. Amplified fragments that have been identified in this way as being different from NGF and BDNF may be sequenced to confirm their identity and, if appropriate, used to obtain the human gene, as described above.

C. In a third preferred version of this embodiment, a human genomic library and human cDNA libraries prepared from a variety of discrete regions of the nervous system may be screened to locate clones containing possible new members of the NGF/BDNF family. Such libraries may be screened either with a portion of the human DNA sequences encoding NGF or BDNF or with one of several synthetic oligonucleotide, approximately 15–40 bases in length, prepared based on various conserved and variable regions of the nucleic acid sequences encoding animal and human NGFs and BDNFs. Reducing the stringency of hybridization during screening of these libraries allows the probes to hybridize not only to clones containing NGF and BDNF sequences but also to clones containing similar, and possibly related, sequences. Screening cDNA libraries from regions of the nervous system that do not contain significant amounts of the messages for NGF and BDNF may be advisable in order to reduce the background of NGF and BDNF clones. Clones identified in these screens may either be sequenced to determine whether they represent the genes for new members of the NGF/BDNF family or they may be further screened, as described in the preceding paragraph, to eliminate those which are likely to represent the genes for the already known members, NGF and BDNF.

Each of the three preferred versions of this embodiment can be used to provide the nucleic acid and inferred amino acid sequences encoding the precursor and mature forms of new human members of the NGF/BDNF family of neurotrophic proteins. This invention encompasses any and all previously-unreported members of the NGF/BDNF family of neurotrophic proteins.

A new member of the NGF/BDNF family of neurotrophic proteins has been identified utilizing the procedures set forth above. As described in Example 4 below and seen in FIG. 6, the complete nucleic acid sequence has been identified that encodes the previously unreported protein NGF-3. Based on the nucleic acid sequence as set forth in FIG. 6 the complete inferred amino acid sequence of mature and precursor NGF-3 has been obtained. The amino acid sequence of NGF-3, inferred by reference to the sequenced NGF-3 gene, is set forth in FIG. 7.

In addition, the invention encompasses neurotrophic proteins of any origin which are biologically equivalent to the neurotrophic proteins described herein.

Throughout this specification, any reference to a neurotrophic protein should be construed to refer to the proteins identified and described herein as members of the NGF/BDNF family of neurotrophic proteins.

By "biologically equivalent" as used throughout the specification and claims, we mean compositions of the present invention which are capable of promoting the survival and maintaining the phenotypic differentiation of nerve or glial cells, but not necessarily to the same degree as the native neurotrophic proteins described herein. By "substantially homologous" as used throughout the ensuing specification and claims, is meant a degree of homology to the native neurotrophic proteins in excess of that displayed by any previously reported neurotrophic proteins. Preferably, the degree of homology is in excess of 70%, most preferably in excess of 80%, and even more preferably in excess of 90%, 95% or 99%. A particularly preferred group of neurotrophic proteins are in excess of 95% homologous with the native proteins. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., specifically incorporated herein by reference. Also included as substantially homologous are those neurotrophic proteins which may be isolated by virtue of cross-reactivity with antibodies to the described protein or whose genes may be isolated through hybridization with the gene or with segments of the described protein.

3. Gene Expression

In one embodiment of the present invention, each of the human genes for members of the NGF/BDNF family of neurotrophic proteins, including the human genes for NGF, BDNF and NGF-3 may be used to establish recombinant expression systems for manufacture of the mature human neurotrophic protein encoded by each gene. In a preferred version of this embodiment, expression may occur in a microorganism, in particular *Escherichia coli*.

The gene for each neurotrophic protein may be modified to facilitate efficient expression in *E. coli*. Such modifications, described in more detail below, may include, but are not limited to, the following: (i) preparation of a DNA sequence that encodes only the inferred mature (processed) form of the protein, by removal of additional coding and non-coding sequences that may be present in the gene; (ii) alteration of human codons to those used preferentially by *E. coli*; (iii) addition of a translational coupler to promote efficient translation in *E. coli*; (iv) insertion of new restriction sites for convenience of subsequent ligation and cloning; and (v) insertion of the DNA into one or more of several expression vectors designed to promote efficient expression of the DNA in *E. coli*. The final expression constructs may be transformed into a suitable strain of *E. coli* and transformants producing mature neurotrophic protein selected for scale-up and manufacture. The expression of NGF in *E. coli*, according to a preferred embodiment of this invention, is described in Example 2 below.

A. General

A natural or synthetic DNA sequence may be used to direct production of such neurotrophic proteins. In one embodiment of the invention, alternate forms of the neurotrophic factors may be produced in which the active site functions in a manner biologically equivalent to that of the neurotrophic proteins described herein. The general expression method comprises:

1. preparation of a DNA sequence capable of directing a host cell to produce a protein having neurotrophic activities or a precursor thereof;
2. cloning the DNA sequence into a vector capable of being transferred into and replicated in a host cell, such vector containing operational elements needed to express the DNA sequence or a precursor thereof;
3. transferring the vector containing the synthetic DNA sequence and operational elements into a host cell capable of expressing the DNA encoding the neurotrophic protein or a precursor thereof;
4. culturing the host cells under the conditions for amplification of the vector and expression of the protein or a precursor thereof;
5. harvesting the protein or a precursor thereof; and
6. permitting the protein to assume an active tertiary structure whereby it possesses or can be processed into a protein having biological activity.

B. DNA Sequences

DNA sequences contemplated for use in this method are discussed in part in Examples 1, 2 and 4. FIG. 6 sets forth the complete nucleic acid sequences coding for human NGF, BDNF, and NGF-3. It is contemplated that these sequences include synthetic and natural DNA sequences and combinations thereof. The natural sequences further include cDNA or genomic DNA segments.

The means for synthetic creation of polynucleotide sequences encoding a protein identical to that encoded by the cDNA or genomic polynucleotide sequences are generally known to one of ordinary skill in the art, particularly in light of the teachings contained herein. As an example of the current state of the art relating to polynucleotide synthesis, one is directed to Matteucci, M. D., and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences described in more detail below or they may contain different nucleotides. In one embodiment, if the synthetic sequences contain nucleotides different from those found in the natural DNA sequences of this invention, it is contemplated that these different sequences will still encode a polypeptide which has the same primary structure as the neurotrophic proteins described herein. In an alternate embodiment, the synthetic sequence containing different nucleotides will encode a polypeptide which has the same biological activity as the neurotrophic proteins described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a human genomic library. An example of such a library useful in this embodiment is set forth by Wyman, et al., (1985) Proc. Nat. Acad. Sci. USA, 82, 2880-2884.

In one version of this embodiment, it is contemplated that the natural DNA sequence will be obtained by a method comprising:

(a) Preparation of a human cDNA library from cells in a vector and a cell capable of amplifying and expressing all or part of that cDNA;

(b) Probing the human DNA library with at least one probe capable of binding to the neurotrophic protein gene or its protein product;

(c) Identifying at least one clone containing the gene coding for the protein by virtue of the ability of the clone to bind at least one probe for the gene or its protein product;

(d) Isolation of the gene or portion of the gene coding for the protein from the clone or clones chosen; and (e) Linking the gene, or suitable fragments thereof, to operational elements necessary to maintain and express the gene in a host cell.

The natural DNA sequences useful in the foregoing process may also be identified and isolated through a method comprising:

(a) Preparation of a human genomic library;

(b) Probing the human genomic library with at least one probe capable of binding a neurotrophic protein gene or its protein product;

(c) Identification of at least one clone containing the gene coding for the protein by virtue of the ability of the clone to bind at least one probe for the gene or its protein product;

(d) Isolation of the gene coding for the protein from the clone or clones identified; and (e) Linking the gene, or suitable fragments thereof, to operational elements to maintain and express the gene in a host cell.

A third potential method for identifying and isolating natural DNA sequences useful in the foregoing process includes the following steps:

(a) Preparation of mRNA from cells that produce the neurotrophic protein;

(b) Synthesizing cDNA (single- or double-stranded) from this mRNA;

(c) Amplifying the neurotrophic protein-specific DNA sequences present in this mixture of cDNA sequences using the polymerase chain reaction (PCR) procedure;

(d) Identifying the PCR products that contain sequences present in the other oligonucleotide probes using Southern blotting analysis;

(e) Subcloning the DNA fragments so identified into vectors that allow direct sequencing of the DNA sequences;

(f) Using these sequences to isolate a cDNA clone from a cDNA library; and (g) Linking the gene, or suitable fragments thereof, to operational elements necessary to maintain and express the gene in host cells.

In isolating a DNA sequence suitable for use in the above-method, it is preferred to identify the two restriction sites located within and closest to the end portions of the appropriate gene or sections of the gene that encode the native protein or fragments thereof. The DNA segment containing the appropriate gene or sections of the gene is then removed from the remainder of the genomic material using appropriate restriction endonucleases. After excision, the 3' and 5' ends of the DNA sequence and any intron exon junctions are reconstructed to provide appropriate DNA sequences capable of coding for the N- and C- termini and the body of the neurotrophic protein and capable of fusing the DNA sequence to its operational elements.

As described in Example 1, the natural DNA sequence coding for human BDNF was identified and isolated by preparing several synthetic oligonucleotides designed by review of the nucleic acid sequence for pig BDNF and utilizing pairs of these primers in the polymerase chain reaction to identify amplified fragments of the human BDNF sequence. The amplified fragments obtained by PCR were then used to clone the complete nucleic acid sequence of human BDNF.

As described in Example 4, the natural DNA sequence coding for human NGF-3 was identified and isolated by preparing synthetic oligonucleotides designed by review of the nucleic acid sequence of human and animal NGF and BDNF and utilizing these primers in the polymerase chain reaction to identify an amplified fragment of the previously unreported human NGF-3 sequence. The amplified fragment obtained by PCR was used to clone the complete nucleic acid sequence of human NGF-3.

C. Vectors

(i). Microorganisms, especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. Preferred vectors are those whose restriction sites have been well documented and which contain the operational elements preferred or required for transcription of the DNA sequence. However, certain embodiments of the present invention are also envisioned which employ currently undiscovered vectors which would contain one or more of the cDNA sequences described herein. In particular, it is preferred that all of these vectors have some or all of the following characteristics: (1) possess a minimal number of host-organism sequences; (2) be stably maintained and propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) a DNA sequence capable of terminating transcription.

In variously preferred embodiments, these cloning vectors containing and capable of expressing the DNA sequences of the present invention contain various operational elements. These "operational elements," as discussed herein, include at least one promoter, at least one Shine-Dalgarno sequence and initiator codon, and at least one terminator codon. Preferably, these "operational elements" also include at least one operator, at least one leader sequence for proteins to be exported from intracellular space, at least one gene for a regulator protein, and any other DNA sequences necessary or preferred for appropriate transcription and subsequent translation of the vector DNA.

Certain of these operational elements may be present in each of the preferred vectors of the present invention. It is contemplated that any additional operational elements which may be required may be added to these vector using methods known to those of ordinary skill in the art, particularly in light of the teachings herein.

In practice, it is possible to construct each of these vectors in a way that allows them to be easily isolated, assembled and interchanged. This facilitates assembly of numerous functional genes from combinations of these elements and the coding region of the DNA sequences. Further, many of these elements will be applicable in more than one host. It is additionally contemplated that the vectors, in certain preferred embodiments, will contain DNA sequences capable of functioning as regulators ("operators"), and other DNA sequences capable of coding for regulator proteins.

(a) Regulators

These regulators, in one embodiment, will serve to prevent expression of the DNA sequence in the presence of certain environmental conditions and, in the presence of other environmental conditions, will allow transcription and subsequent expression of the protein coded for by the DNA sequence. In particular, it is preferred that regulatory segments be inserted into the vector such that expression of the DNA sequence will not occur, or will occur to a greatly reduced extent, in the absence of, for example, isopropylthio-beta-D-galactoside. In this situation, the transformed microorganisms containing the DNA sequence may be grown to a desired density prior to initiation of the expression of the neurotrophic protein. In this embodiment, expression of the desired protein is induced by addition of a substance to the microbial environment capable of causing expression of the DNA sequence after the desired density has been achieved.

(b) Promoters

The expression vectors must contain promoters which can be used by the host organism for expression of its own proteins. While the lactose promoter system is commonly used, other microbial promoters have been isolated and characterized, enabling one skilled in the art to use them for expression of the recombinant neurotrophic protein.

(c) Transcription Terminator

The transcription terminators contemplated herein serve to stabilize the vector. In particular, those sequences as described by Rosenberg, M. and Court, D., in Ann. Rev. Genet. 13:319-353 (1979), specifically incorporated herein by reference, are contemplated for use in the present invention.

(d) Non-Translated Sequence

It is noted that, in the preferred embodiment, it may also be desirable to reconstruct the 3' or 5' end of the coding region to allow incorporation of 3' or 5' non-translated sequences into the gene transcript. Included among these non-translated sequences are those which stabilize the mRNA as they are identified by Schmeissner, U., McKenney, K., Rosenberg, M and Court, D. in J. Mol. Biol. 176:39-53 (1984), specifically incorporated herein by reference.

(e) Ribosome Binding Sites

The microbial expression of foreign proteins requires certain operational elements which include, but are not limited to, ribosome binding sites. A ribosome binding site is a sequence which a ribosome recognizes and binds to in the initiation of protein synthesis as set forth in Gold, L., et al., Ann. Rev. Microbio. 35:557-580; or Marquis, D. M., et al., Gene 42:175-183 (1986), both of which are specifically incorporated herein by reference. A preferred ribosome binding site is GAGGC-GCAAAAA(ATG).

(f) Leader Sequence and Translational Coupler

Additionally, it is preferred that DNA coding for an appropriate secretory leader (signal) sequence be present at the 5' end of the DNA sequence as set forth by Watson, M. E. in Nucleic Acids Res. 12:5145-5163, specifically incorporated herein by reference, if the protein is to be excreted from the cytoplasm. The DNA for the leader sequence must be in a position which allows the production of a fusion protein in which the leader sequence is immediately adjacent to and covalently joined to the neurotrophic protein, i.e., there must be no transcription or translation termination signals between the two DNA coding sequences. The presence of the leader sequence is desired in part for one or more of the following reasons. First, the presence of the leader sequence may facilitate host processing of the neurotrophic protein. In particular, the leader sequence may direct cleavage of the initial translation product by a leader peptidase to remove the leader sequence and leave a polypeptide with the amino acid sequence which has potential protein activity. Second, the presence of the leader sequence may facilitate purification of the neurotrophic protein, through directing the protein out of the cell cytoplasm. In some species of host microorganisms, the presence of an appropriate leader sequence will allow transport of the completed protein into the periplasmic space, as in the case of some E. coli. In the case of certain E. coli, Saccharomyces and strains of Bacillus and Pseudomonas, the appropriate leader sequence will allow transport of the protein through the cell membrane and into the extracellular medium. In this situation, the protein may be purified from extracellular protein. Thirdly, in the case of some of the proteins prepared by the present invention, the presence of the leader sequence may be necessary to locate the completed protein in an environment where it may fold to assume its active structure, which structure possesses the appropriate protein activity.

In one preferred embodiment of the present invention, an additional DNA sequence is located immediately preceding the DNA sequence which codes for the neurotrophic protein. The additional DNA sequence is capable of functioning as a translational coupler, i.e., it is a DNA sequence that encodes an RNA which serves to position ribosomes immediately adjacent to the ribosome binding site of the protein RNA with which it is contiguous. In one embodiment of the present invention, the translational coupler may be derived using the DNA sequence

TAACGAGGCGCAAAAAATGAAAAAGACAGCTATCGCGATCTTGGAGGATGATTAAATG and methods currently known to those of ordinary skill in the art related to translational couplers.

(g) Translation Terminator

The translation terminators contemplated herein serve to stop the translation of mRNA. They may be either natural, as described by Kohli, J., Mol. Gen. Genet. 182:430–439; or synthesized, as described by Pettersson, R. F. Gene 24:15–27 (1983), both of which references are specifically incorporated herein by reference.

(h) Selectable Marker

Additionally, it is preferred that the cloning vector contain a selectable marker, such as a drug resistance marker or other marker which causes expression of a selectable trait by the host microorganism. In one embodiment of the present invention, the gene for ampicillin resistance is included in the vector while, in other plasmids, the gene for tetracycline resistance or the gene for chloramphenicol resistance is included.

Such a drug resistance or other selectable marker is intended in part to facilitate in the selection of transformants. Additionally, the presence of such a selectable marker in the cloning vector may be of use in keeping contaminating microorganisms from multiplying in the culture medium. In this embodiment, a pure culture of the transformed host microorganisms would be obtained by culturing the microorganisms under conditions which require the induced phenotype for survival.

The operational elements as discussed herein are routinely selected by those of ordinary skill in the art in light of prior literature and the teachings contained herein. General examples of these operational elements are set forth in B. Lewin, Genes, Wiley & Sons, New York (1983), which is specifically incorporated herein by reference. Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

Figure 4:
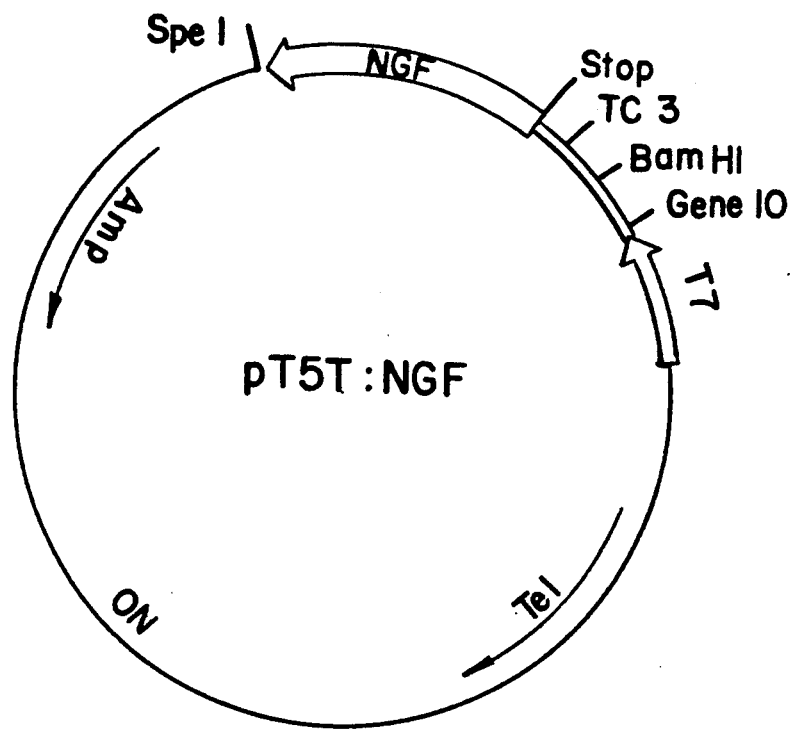
FIG. 4 depicts certain features of the bacterial expression vector pT5T. Features are representative only and not drawn to exact scale. The NGF insert is intended to represent any member of the NGF/BDNF family of neurotrophic proteins.
Figure 5:
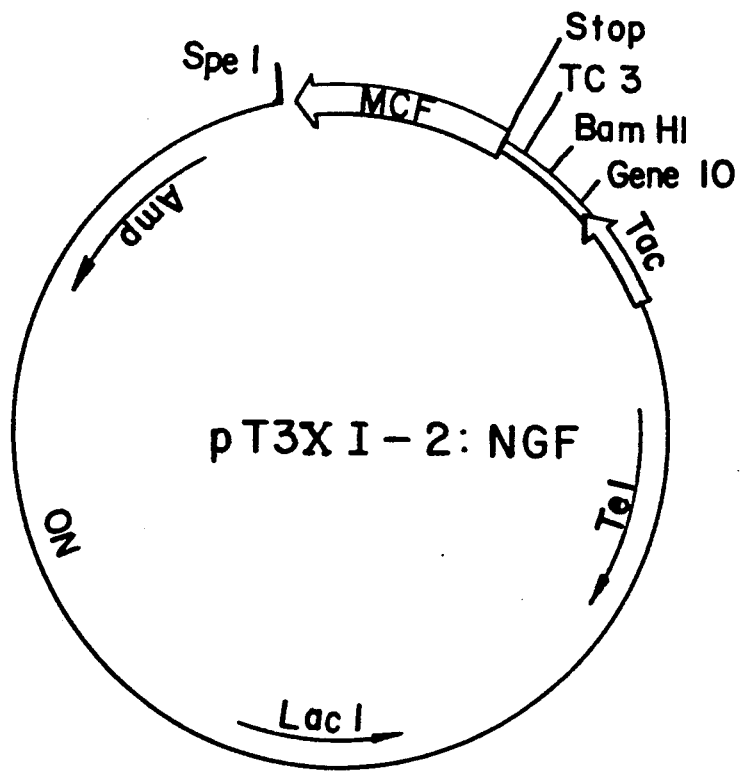
FIG. 5 depicts certain features of the bacterial expression vector pT3XI-2. Features are representative only and not drawn to exact scale. The NGF insert is intended to represent any member of the NGF/BDNF family of neurotrophic proteins.

In Example 2 below, the preparation of two vectors containing the nucleic acid sequence coding for mature human NGF is described. The vectors into which the appropriate nucleic acid sequences were inserted are *E. Coli* expression vectors referred to as pT5T and pT3XI-2. Details of the vector pT5T:NGF are shown in FIG. 4 and details of the vector pT3XI-2:NGF are shown in FIG. 5.

In construction of the cloning vectors of the present invention, it should additionally be noted that multiple copies of the DNA sequence and its attendant operational elements may be inserted into each vector. In such an embodiment, the host organism would produce greater amounts per vector of the desired neurotrophic protein. The number of multiple copies of the DNA sequence which may be inserted into the vector is limited only by the ability of the resultant vector, due to its size, to be transferred into and replicated and transcribed in an appropriate host cell.

(ii) Other Microorganisms

Vectors suitable for use in microorganisms other *E. coli* are also contemplated for this invention. Such vectors are described in Table 1. In addition, certain preferred vectors are discussed below.

TABLE 1

| HOSTS | REGULATED PROMOTERS | INDUCER | TRANSCRIPTIONAL TERMINATOR | TRANSCRIPTION STABILIZATION | MRNA | START SITE & LEADER PEPTIDE | RS MARKER | BINDING SITE |
|---|---|---|---|---|---|---|---|---|
| E. coli | Lac[1], Tac[2] | IPTG | rrnB[6] increased | ompA[8] | bla[11] rrnC[7] | ampicillin[14] lambda ompA[12] int[9] | tetracycline[14,15] | |
| | Lambda pL | | | | | | | |
| | Trp[5] | temperature IAA addition or tryptophan depletion | | | trp[10] | phoS | chloramphenical[16] | |
| Bacillus | *alpha | E. coli rrn | amylase[17] *subtilisin[18] *p-43[19] spac-I[26] IPTG | rrn BT.T[20] | B. amy neutral | B.amy alpha-amylase B.subt. subtilisin[23] | Kan[r 24] protease[21] Cam[r 25] | B. amy neural protease B.amy alpha-amylase[22] |
| Pseudomonas | Trp[27] (*E. coil*) Lac(*E. coli*) Tac(*E. coli*) | IAA addition, or tryptophan depletion | | IPTG | | phospholipase C28 exotoxin A[28] | sulfonamide[30] strepto-mycin[30] | Trp (*E. coil*) |
| Yeast | Gal 1[31,] | Glucose 10[32] Adh, I[33,] II[34] Pho 5 | Cyc1 depletion and galactose Glucose Sac 2 depletion Phosphate | Invertase[36] Una Alpha factor | | Ura 3[37] Acid phosphatase[36] Tap 1 | Leu 2[38] Alpha Factor His 3 | |

TABLE 1-continued

| HOSTS | REGULATED PROMOTERS | INDUCER | TRANSCRIPTIONAL TERMINATOR | TRANSCRIPTION STABILIZATION | MRNA | START SITE & LEADER PEPTIDE | MARKER | RS BINDING SITE |
|---|---|---|---|---|---|---|---|---|
| | | depletion | | | | | | |

*non-regulated

[1] Backman, K., Ptashne, M. and Gilbert, W. Proc. Natl. Acad. Sci. USA 73, 4174–4178 (1976).
[2] de Boer, H.A., Comstock, L.J., and Vasser, M. Proc. Natl. Acad. Sci USA 80, 21–25 (1983).
[3] Shimatake, H. and Rosenberg, M. Nature 292, 128–132 (1981).
[4] Derom, C., Gheysen, D. and Fiers, W. Gene 17, 45–54 (1982).
[5] Hallewell, R.A. and Emtage, S. Gene 9, 27–47 (1980).
[6] Brosius, J., Dull, T.J., Sleeter, D.D. and Noller, H.F. J. Mol. Biol. 148 107–127 (1981).
[7] Normanly, J., Ogden, R.C., Horvath, S.J. and Abelson, J. Nature 321, 213–219 (1986).
[8] Belasco, J.G., Nilsson, G., von Gabain, A. and Cohen, S.N. Cell 46, 245–251 (1986).
[9] Schmeissner, U., McKenney, K., Rosenberg M. and Court, D. J. Mol. Bio. 176, 39–53 (1984).
[10] Mott, J.E., Galloway, J.L. and Platt, T. EMBO J. 4, 1887–1891 (1985).
[11] Koshland, D. And Botstein, D. Cell 20, 749–760 (1980).
[12] Movva, N.R., Kakamura, K. and Inouye, M. J. Mol. Biol. 143, 317–328 (1980).
[13] Surin, B.P., Jans, D.A., Fimmel, A.L., Shaw, D.C., Cox, G.B. and Rosenberg, H. J. Bacteriol. 157, 772–778 (1984).
[14] Sutcliffe, J.G. Proc. Natl. Acad. Sci. USA 75, 3737–3741 (1978).
[15] Peden, K.W.C. Gene 22, 277–280 (1983).
[16] Alton, N.K. and Vapnek, D. Nature 282, 864–869 (1979).
[17] Yang, M., Galizzi, A., and Henner, D. Nuc. Acids Res. 11(2), 237–248 (1983).
[18] Wong, S.-L., Price C.W., Goldfarb, D.S., and Doi, R.H. Proc. Natl. Acad. Sci. USA 81, 1184–1188 (1984).
[19] Wang, P.-Z. and Doi, R.H. J. Biol. Chem. 251, 8619–8625, (1984).
[20] Lin, C.-K., Quinn, L.A., Rodriguez, R.L. J. Cell Biochem. Suppl. (9B), p. 198 (1985).
[21] Vasantha, N., Thompson, L.D., Rhodes, C., Banner, C., Nagle, J., and Filpula, D. J. Bact. 159(3), 811–819 (1984).
[22] Plava, I., Sarvas, M., Lehtovaara, P., Sibazkov, M., and Kaariainen, L. Proc. Natl. Acad. Sci. USA 79, 5582–5586 (1982).
[23] Wong, S.-L., Pricee, C.W., Goldfarb, D.S., and Doi, R.H. Proc. Natl. Acad. Sci. USA 81, 1184–1188 (1984).
[24] Sullivan, M.A., Yasbin, R.E., Young, F.E. Gene 29, 21–46 (1984).
[25] Vasantha, N., Thompson, L.D., Rhodes, C., Banner, C. Nagle, J., and Filula, D.J. Bact. 159(3), 811–819 (1984).
[26] Yansura, D.G. and Henner, D. J. PNAS 81, 439–443 (1984).
[27] Gray, G.L., McKeown, K.A., Jones, A.J.S., Seeburg, P.H. and Heyneker, H.L. Biotechnology, 161–165 (1984).
[28] Lory, S., and Tai, P.C. Gene 22, 95–101 (1983).
[29] Liu, P.V. J. Infect. Dis. 130 (suppl), 594–599 (1974).
[30] Wood, D.G., Hollinger, M.F., and Tindol, M.B. J. Bact. 145, 1448–1451 (1981).
[31] St. John, T.P. and Davis, R.W. J. Mol. Biol. 152, 285–315 (1981).
[32] Hopper, J.E., and Rowe, L.B. J. Biol. Chem. 253, 7566–7569 (1978).
[33] Denis, C.L., Ferguson, J. and Young, E.T. J. Biol. Chem. 258, 1165–1171 (1983).
[34] Lutsdorf, L. and Megnet, R. Archs. Biochem. Biophys. 126, 933–944 (1968).
[35] Meyhack, B., Bajwa, N., Rudolph, H. and Hinnen, A. EMBO. J. 6, 675–680 (1982).
[36] Watson, M.E. Nucleic Acid Research 12, 5145–5164 (1984).
[37] Gerband, C. and Guerineau, M. Curr. Genet. 1, 219–228 (1980).
[38] Hinnen, A., Hicks, J.B. and Fink, G.R. Proc. Natl. Acad. Sci. USA 75, 1929–1933 (1978).
[39] Jabbar, M.A., Sivasubramanian, N. and Nayak, D.P. Proc. Natl. Acad. Sci. USA 82, 2019–2023 (1985).

Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. in Biotechnology, May, 1983, pp. 269–275; Panopoulos, N.J. in *Genetic Engineering in the Plant Sciences*, Praeger Publishers, New York, N.Y., pp. 163–185 (1981); and Sakagucki, K. in Current Topics in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A. eds., Elsevier/North Holland Biomedical Press (1979), specifically incorporated herein by reference. The advantages of RSF1010 are that it is a relatively small, high copy number plasmid which is readily transformed into and stably maintained in both E. coli and Pseudomonas species. In this system, it would be preferred to use the Tac expression system as described for Escherichia, since it appears that the E. coli trp promoter is readily recognized by Pseudomonas RNA polymerase as set forth by Sakagucki, K. in Current Topics in Microbiology and Immunology 96:31–45 (1982) and Gray, G. L., McKeown, K. A., Jones A. J. S., Seeburg, P. H., and Heyneker, H. L. in Biotechnology, February 1984, pp. 161–165, both of which are specifically incorporated herein by reference. Transcriptional activity may be further maximized by requiring the exchange of the promoter with, e.g., an E. coli or P. aeruoinosa trp promoter. Additionally, the lacI gene of E. coli would also be included in the plasmid to effect regulation.

Translation may be coupled to translation initiation for any of the Pseudomonas proteins, as well as to initiation sites for any of the highly expressed proteins of the type chosen to cause intracellular expression of the neurotrophic protein.

In those cases where restriction minus strains of a host Pseudomonas species are not available, transformation efficiency with plasmid constructs isolated from E. coli are poor. Therefore, passage of the Pseudomonas cloning vector through an r− m+ strain of another species prior to transformation of the desired host, as set forth in Bagdasarian, M., et al., *Plasmids of Medical, Environmental and Commercial Importance*, pp. 411–422, Timmis and Puhler eds., Elsevier/North Holland Biomedical Press (1979), specifically incorporated herein by reference, is desired.

(b) Bacillus Vectors

Furthermore, a preferred expression system in hosts of the genus Bacillus involves using plasmid pUB110 as the cloning vehicle. As in other host vector systems, it is possible in Bacillus to express the neurotrophic proteins of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, New York, pp. 115-131 (1980), specifically incorporated herein by reference. For the expression and secretion of the neurotrophic proteins from *B. subtilis*, the signal sequence of alpha-amylase is preferably coupled to the coding region for the protein. For synthesis of intracellular protein, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilii*, Ganesan, A. T. and Hoch, J. A., eds., Academic Press, pp. 249-263 (1984), specifically incorporated by reference. The lacI gene of *E. coli* would also be included in the plasmid to effect regulation.

(c) Colstridium Vectors

One preferred construction for expression in Clostridium is in plasmid pJU12, described by Squires, C. H. et al., in J. Bacteriol. 159:465-471 (1984) and specifically incorporated herein by reference, transformed into *C. perfringens* by the method of Heefner, D. L. et al., as described in J. Bacteriol. 159:460-464 (1984), specifically incorporated herein by reference. Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

(d) Yeast Vectors

Maintenance of foreign DNA introduced into yeast can be effected in several ways as described by Botstein, D. and Davis, R. W., in *The Molecular Biology of the Yeast Saccharomyces,* Cold Spring Harbor Laboratory, Strathern, Jones and Broach, eds., pp. 607-636 (1982), specifically incorporated herein by reference. One preferred expression system for use with host organisms of the genus Saccharomyces harbors the neurotrophic protein gene on the 2 micron plasmid. The advantages of the 2 micron circle include relatively high copy number and stability when introduced into cir' strains. These vectors preferably incorporate the replication origin and at least one antibiotic resistance marker from pBR322 to allow replication and selection in *E. coli.* In addition, the plasmid will preferably have the two micron sequence and the yeast LEU2 gene to serve the same purposes in LEU2 defective mutants of yeast.

If it is contemplated that the recombinant neurotrophic proteins will ultimately be expressed in yeast, it is preferred that the cloning vector first be transferred into *Escherichia coli,* where the vector would be allowed to replicate and from which the vector would be obtained and purified after amplification. The vector would then be transferred into the yeast for ultimate expression of the protein.

(iii) Mammalian Cells

The cDNA for the neurotrophic protein will serve as the gene for expression of the protein in mammalian cells. It should have a sequence that will be efficient at binding ribosomes such as that described by Kozak, in Nucleic Acids Research 15:8125-8132 (1987), specifically incorporated herein by reference, and should have coding capacity for a leader sequence (see section 3(a)(vi)) to direct the mature protein out of the cell in a processed form. The DNA restriction fragment carrying the complete cDNA sequence can be inserted into an expression vector which has a transcriptional promoter and a transcriptional enhancer as described by Guarente, L. in Cell 52:303-305 (1988) and Kadonaga, J. T. et al., in Cell 51:1079-1090 (1987), both of which are specifically incorporated herein by reference. The promoter may be regulatable as in the plasmid pMSG (Pharmacia Cat. No. 27450601) if constitutive expression of the protein is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection in *E. coli.*

In order to select a stable cell line that produces the neurotrophic proteins, the expression vector can carry the gene for a selectable marker such as a drug resistance marker or carry a complementary gene for a deficient cell line, such as a dihydrofolate reductase (dhfr) gene for transforming a dhfr. cell line as described by Ausubel et al., supra. Alternatively, a separate plasmid carrying the selectable marker can be cotransformed along with the expression vector.

D. Host Cells/Transformation

The vector thus obtained is transferred into an appropriate host cell. These host cells may be microorganisms or mammalian cells. In the preferred embodiment of this invention the host cells utilized are microorganisms, and more specifically are *E. coli* cells.

(i) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. Examples of such methods may be found in Advanced Bacterial Genetics by R. W. Davis et al., Cold Spring Harbor Press, Cold Spring Harbor, N.Y. (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the foreign genes.

It is preferred that the host microorganism be a facultative anaerobe or an aerobe. Particular hosts which may be preferable for use in this method include yeasts and bacteria. Specific yeasts include those of the genus Saccharomyces, and especially *Saccharomyces cerevisiae*. Specific bacteria include those of the genera Bacillus, Escherichia, and Pseudomonas, especially *Bacillus subtilis* and *Escherichia coli*. Additional host cells are listed in Table I, supra.

(ii) Mammalian Cells

The vector can be introduced into mammalian cells in culture by several techniques such as calcium phosphate: DNA coprecipitation, electroporation, or protoplast fusion. The preferred method is coprecipitation with calcium phosphate as described by Ausubel et al., supra.

Many stable cell types exist that are transformable and capable of transcribing and translating the cDNA sequence, processing the precursor neurotrophic proteins and secreting the mature protein. However, cell types may be variable with regard to glycosylation of secreted proteins and post-translational modification of amino acid residues, if any. Thus, the ideal cell types are those that produce a recombinant neurotrophic protein identical to the natural molecule.

E. Culturing Engineered Cells

The host cells are cultured under conditions appropriate for the expression of the neurotrophic proteins. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Harbor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression of the DNA sequence. When optimal cell density is approached, the environmental conditions are altered to those appropriate for expression of the DNA sequence. It is thus contemplated that the production of the neurotrophic proteins will occur in a time span subsequent to the growth of the host cells to near optimal density, and that the resultant protein will be harvested at some time after the regulatory conditions necessary for its expression were induced.

4. Renaturing of Expressed Recombinant Proteins

In a preferred embodiment of the present invention, the recombinant mature neurotrophic proteins are purified subsequent to harvesting and prior to assumption of their active structure. This embodiment is preferred as the inventors believe that recovery of a high yield of re-folded protein is facilitated if the protein is first purified. However, in one preferred, alternate embodiment, the neurotrophic protein may be allowed to refold to assume its active structure prior to purification. In yet another preferred, alternate embodiment, the protein is present in its re-folded, active state upon recovery from the culturing medium.

In certain circumstances, the mature neurotrophic protein will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein.

In one embodiment of the present invention, the protein produced in microorganisms may lack substantial biological activity and will need to be refolded and renatured to provide a neurotrophic protein with a biological specific activity expected of members of the NGF/BDNF family. The expected specific activity is either that observed for the protein expressed in eukaryotic cells or that observed for the same or a related protein purified from natural sources (e.g., mouse submaxillary gland NGF and pig brain BDNF).

Often the lack of biological activity in proteins expressed in microorganisms is related to improper formation of intramolecular disulfide bonds. In a preferred version of this embodiment, the recombinant neurotrophic protein produced in *E. coli* may be refolded and renatured to attain the correct configuration of intramolecular disulfide bonds and the expected biological specific activity.

In a preferred version, the recombinant protein may be refolded and renatured by using the following steps:

(1) Any intramolecular or intermolecular disulfide bonds and/or any noncovalent interactions which have occurred involving the mature neurotrophic protein produced in a microorganism are first disrupted. In order to do this, the protein is exposed to sufficient denaturant (for example, guanidine hydrochloride or urea) and sufficient reducing agent (for example, beta-mercaptoethanol, dithiothreitol, or cysteine) to denature the protein, disrupt noncovalent interactions, and reduce disulfide bonds.

(2) After the mature neurotrophic protein has been denatured and reduced, the free thiols present in the reduced protein are oxidized by addition of a large excess of disulfide-containing reagent (for example, glutathione or cystine). This reaction produces mixed disulfide bonds in which each cysteine residue in the mature neurotrophic protein forms a disulfide bond with the monomeric form of the oxidizing agent. This step helps to prevent the formation of incorrect intramolecular disulfide bonds in the neurotrophic protein during subsequent processing.

(3) The denaturant and oxidizing agent are then diluted to a defined concentration and a thiol-containing reagent (for example, cysteine) is added to catalyze disulfide interchange. The objective is to produce an environment in which the denaturant concentration is sufficiently reduced to allow the neurotrophic protein to assume various 3-dimensional configurations and in which the oxidization/reduction potential is adjusted to allow the formation and breaking of disulfide bonds. It is presumed that the proper 3-dimensional structure and disulfide bonding pattern of the mature neurotrophic protein is energetically more stable than other possible conformations. Therefore, conditions in which the neurotrophic protein is allowed to assume a variety of 3-dimensional conformations and intramolecular disulfide bond patterns, will allow a significant proportion of the neurotrophic protein to reform the correct intramolecular disulfide bonding pattern, the correct 3-dimensional structure, and, therefore, to become biologically active.

These procedures are mild and should not result in the chemical modification of the neurotrophic protein. If urea is used as a denaturant in the protocol, it is important to remove any cyanate that may form, by passing the urea solution over an anion exchange column, such as DOWEX 1-X8(BioRad). If cyanate is not removed, it can modify amino groups in the protein (Stark 1967 *Methods in Enzymology* 11:125).

The optimal concentration and choice of denaturant, oxidizing reagent, thiol reagents and their concentrations in the final refolding solution are determined experimentally by monitoring the proportion of neurotrophic protein properly refolded and biologically active. The objective in the final refolding solution is to provide a controlled environment in which disulfide interchange and conformational changes can occur in the neurotrophic protein until the favored conformation and disulfide boding pattern is achieved. The conditions for optimal refolding are expected to be substantially the same for all members of the NGF/BDNF family of neurotrophic proteins, since they are closely related in amino acid sequence, including the relative location of all six cysteine residues in the mature protein, and, therefore, presumably assume the same disulfide bonding pattern.

Example 3 below describes an experiment showing that this refolding protocol is successful for refolding mature NGF produced in bacteria as follows: (1) Correctly folded and fully-biologically active mature NGF, either produced in a eukaryotic cell expression system or purified from natural sources, is denatured and disulfide bonds reduced, as described above, causing a loss of biological activity. Since the NGF was biologically active before denaturation and reduction, it is possible to demonstrate the denaturation and refolding has occurred by the loss of biological activity; (2) The denatured and reduced NGF is renatured according to the protocol described herein to determine that biological activity has been restored. It is presumed that restoration of biological activity is dependent on proper refolding and renaturation of the denatured and reduced protein. It is asserted that mature NGF from any of the sources indicated above, including a bacterial cell expression system, would be structurally indistinguishable after denaturation and reduction. Therefore, successful refolding of denatured and reduced mature NGF from either a eukaryotic cell expression system or from natural sources, indicates that mature NGF produced in bacterial cells can be successfully refolded (see Example 3 and FIG. 3).

Example 3B describes the successful refolding of mature NGF produced in a bacterial expression system using *E. coli*, using methods similar to those described above. The refolded NGF is fully biologically active and migrates at the position of native, insect cell-produced NGF on reversed-phase high performance liquid chromatography.

5. Purification of the Recombinant Neurotrophic Protein

The protocol described above to refold and renature the mature neurotrophic protein may be applied at a stage during purification of the recombinant protein which is most convenient and which has been determined by experience to produce a high yield of biologically active protein.

In one embodiment of the present invention, recombinant members of the NGF/BDNF family may be purified from extracts of the expression host cell by standard techniques of protein chemistry until the recombinant protein is sufficiently pure to be used in pharmaceutical preparations. In a preferred embodiment the procedures to be used for purification of the recombinant protein may include, but are not limited to, some or all of the following: ion exchange chromatography (e.g., Q-, S-, and DEAE- Sepharose ion exchange columns), gel permeation chromatography (e.g. Superose sizing columns), chromatofocusing (e.g. Mono-P columns), hydrophobic interaction chromatography (e.g., octyl- and phenyl-Sepharose HIC columns), affinity chromatography (e.g., zinc, copper, and mercury metal-affinity columns).

6. Formulation of Pharmaceutical Products

As indicated previously, the neurotrophic proteins of the present invention are contemplated for use as therapeutic agents and thus are to be formulated in pharmaceutically acceptable carriers. In one embodiment of the present invention, the neurotrophic proteins may be chemically modified to improve the pharmacokinetic properties of the molecules. An example would be the attachment of high molecular weight polymeric materials, such as polyethylene glycol, to the neurotrophic protein. The neurotrophic proteins may be administered separately, in combination with other members of the NGF/BDNF family of neurotrophic proteins, or in combination with other neurotrophic proteins or other therapeutic agents, depending on the type of nerve cell disorder being treated.

EXAMPLE 1

Isolation, Sequencing and Expression of the Human Gene for BDNF

A. Use of the Polymerase Chain Reaction to Amplify Portions of the Human BDNF Gene The following oligonucleotides were synthesized based on the reported nucleic acid sequence for pig BDNF (Leibrock et al. 1989 ibid.):

BDNF-1 [non-degenerate, sense strand oligo located immediately upstream of the fifth coding base in pig BDNF, also containing a 5' BamHI site]
5' GGA TCC GGT GAG AAG AGT GAT GAC 3'
BDNF-2 [partially degenerate guessmer, sense strand oligo running downstream from the initiation codon for pig BDNF; this oligo was synthesized in two different pools to reduce degeneracy]
BDNF-2A
5' ATG ACN ATC/A/T CTG TTT/C CTG ACN ATG 3'
BDNF-2B
5' ATG ACN ATC/A/T CTG TTT/C CTC ACN ATG 3'
BDNF-3 [non-degenerate, anti-sense strand oligo located immediately downstream of the termination codon for pig BDNF, also containing a 5' SpeI site]
5' ACT AGT TAA TCT ATA CAA CAT AAA GCC 3'
BDNF-4 [partially degenerate guessmer, anti-sense strand oligo running upstream from the termination codon for pig BDNF]
5' ATN GTG/C AGN GTA/G CAN ACA/G CA 3'
BDNF-5 [degenerate, sense strand oligo located in the coding region for the mature (processed) BDNF protein]
5' GAT/C AAA/G AAA/G ACN GCN GTN GAT/C ATG 3'

PCR reactions were performed using human genomic DNA as template and the following combinations of synthetic oligonucleotides as primers: BDNF-1 and BDNF-3; BDNF-2A and BDNF-3; BDNF-2B and BDNF-3; BDNF-2A and BDNF-4; BDNF-2B and BDNF-4; and, BDNF-1 and BDNF-4. The reaction products were electrophoresed and DNA (Southern) blots were probed with radiolabeled BDNF-5 to identify amplified fragments likely to correspond to human BDNF. See Experimental Appendix in this Example for details.

There were bands at approximately the expected size that hybridized to BDNF-5 in the reactions using BDNF-1/BDNF-3, BDNF-2A/BDNF-3, and BDNF-2B/BDNF-3 as primers. The DNA at the position of the hybridizing Southern band from the electrophoresed BDNF-1/BDNF-3 reaction mixture was cut out of the gel and an aliquot was sequenced directly using BDNF-1 and BDNF-3 as sequencing primers to give a partial sequence of the human gene in the coding region for BDNF (FIG. 1). The remainder of this amplified DNA was subcloned into SmaI-cut phage M13mp10 and positive subclones selected based on hybridization to radiolabeled BDNF-5. Two independent positive subclones in opposite orientations, BDNF-PCR1 & 2, were sequenced to give the sequence of the human gene in the coding region for BDNF (FIG. 1).

B. Use of DNA Amplified With PCR to Clone the Human Gene for BDNF

DNA at the position of the amplified hybridizing Southern band was radiolabeled and used to screen a human genomic DNA library in phage lambda EMBL3 and 6 positive clones were plaque purified. The DNA from clone #3 was digested separately with the following restriction enzymes: HinfI; AluI; RsaI; and, NcoI/Sau3AI. These enzymes were chosen because they break the BDNF coding sequence into several fragments suitable in size for cloning into M13. Restriction fragments containing BDNF coding sequence were subcloned into phage M13mp10 and sequenced to confirm the sequence of the human gene in the region coding for BDNF (FIG. 1). FIG. 1 also shows the inferred amino acid sequence of the precursor and mature (processed) human BDNF protein. The cleavage site proposed in FIG. 1 is based on the similarities of the cleavage sites in the known sequences of NGF and pig BDNF and the known amino acid sequences of NGF and pig BDNF.

The BDNF sequence obtained from PCR amplified fragments (FIG. 1) and from two human genomic DNA clones differed in nucleic acid position 196. The human genomic clone had an A in place of G at position 196, which changes amino acid 66 from valine to methionine. This difference occurs in the precursor, not the mature, biologically-active form of BDNF. This change of a single base pair and a single amino acid may represent an allelic difference in the BDNF sequence within the human genome.

Sequencing of an additional clone gave a sequence identical to that shown in FIG. 1, except that the amino acid at position 223 was lysine (K) instead of arginine (R) and the codon was AAA instead of AGA. This difference occurs in the mature biologically-active active form of human BDNF. This may represent an alternate human allele at this position.

C. Expression of Biologically Active BDNF in COS-7 Cells

In order to confirm that the human BDNF gene we obtained actually coded for biologically active BDNF, the gene was expressed transiently in COS-7 cells and the expressed material was assayed for the ability to promote the survival of embryonic day 10 chick dorsal root ganglion neurons in culture, a known property of BDNF purified from pig brains (Barde et al. 1982 *The EMBO Journal* 1:549).

1. Preparation of a DNA Construct for the Expression of Human BDNF

The gel-purified DNA containing the human BDNF coding sequence, amplified from human genomic DNA by PCR with oligonucleotides BDNF-1 and BDNF-3 was ligated into the COS cell expression vector pSG5 (Green et al. 1988 *Nuc. Acids Res.* 16:369). Plasmid pSG5 was digested with restriction endonucleases EcoRI and BamHI and the cohesive ends were made blunt by treatment with the Klenow fragment of DNA polymerase I in the presence of all four deoxyribonucleotides. The gel-purified DNA containing the entire BDNF coding sequence was then ligated into the blunt-ended pSG5. The orientation of inserted DNA in which the BDNF precursor protein can be expressed from the SV40 immediate early promoter upon transfection into COS cells was identified by restriction mapping. In the desired orientation, the BDNF insert can be separated from the vector following digestion with BamHI and BglII.

2. Transfection of COS Cells

DNA from pSG5 with and without the BDNF coding insert was prepared by the method of alkaline lysis followed by CsCl density centrifugation (Maniatis et al., ibid.). The plasmid DNA was transfected into COS-7 cells using lipofectin according to protocol C of the manufacturer's instructions (BRL). COS cell cultures transfected with plasmid DNA without a BDNF coding insert served as a negative control.

3. Bioassay of Expressed Materials

Figure 8:
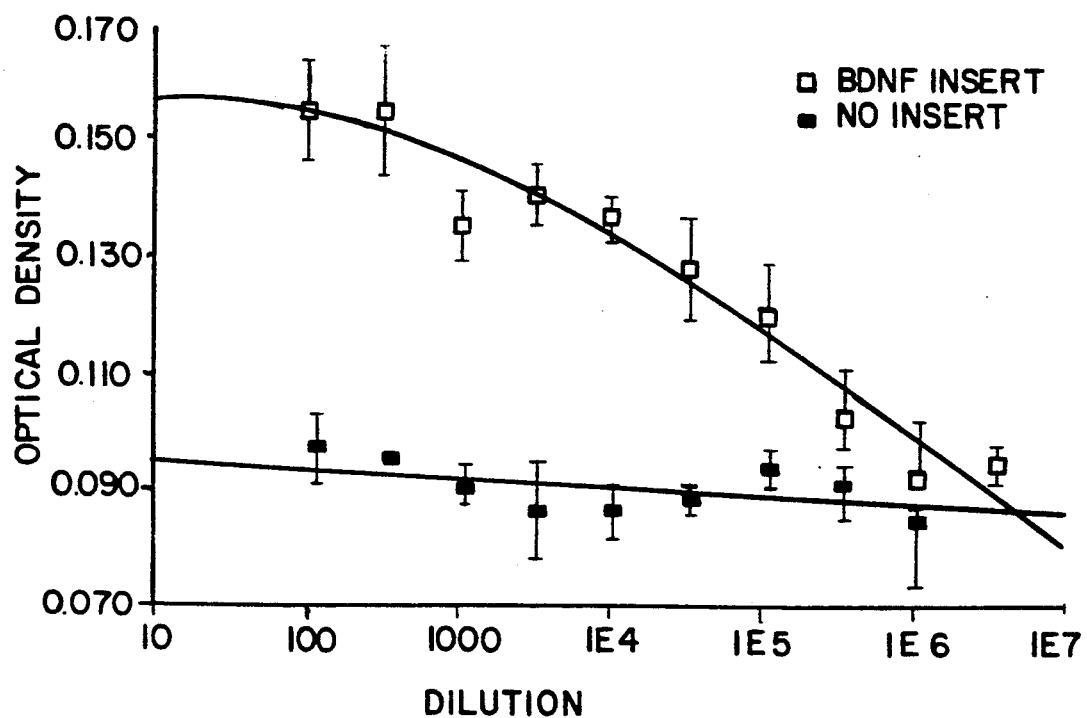
FIG. 8 depicts the bioassay using E10 chick dorsal root ganglion neurons of extracts of COS-7 cells transfected with plasmid pSG5 with and without a human BDNF insert.

Twenty-four hours after transfection the cells were scraped off the dish and harvested by brief centrifugation. Cell pellets were extracted by brief sonication on ice in 20 mM sodium phosphate, pH 6.7 containing 1 mM EDTA, 0.1 mM PMSF, and 0.1 µM pepstatin. Serial dilutions of the cell extract from each culture were assayed for bioactivity using chick embryo day 10 dorsal root ganglion neurons (see Experimental Appendix to Example 3). There was significant biological activity detected in the extract of cells transfected with pSG5 containing the BDNF insert, but not in the extract of cells transfected with pSG5 without an insert (FIG. 8). These results indicate that the gene we have cloned is capable of expressing a biologically active BDNF.

D. Expression of Mature Human BDNF in *E. coli*

The human mature BDNF gene, as described in FIG. 1, is inserted into *E. coli* expression vectors, such vectors are introduced into *E. coli* host cells, and expression of the gene to produce human mature BDNF is accomplished according to the procedures described in Example 2 below by replacing the BDNF gene for the NGF gene.

EXPERIMENTAL APPENDIX TO EXAMPLE 1

1. Molecular Biology Methods

The polymerase chain reaction (PCR) was performed essentially as described in Saiki et al, 1988 Science 239: 487. PCR reaction products were electrophoresed through 2% agarose gels and transferred onto Zeta-Bind membranes (BioRad) for DNA (Southern) blotting. Appropriate amplified bands were cut from original gels and prepared for subcloning by repairing the ends with the Klenow fragment of DNA polymerase (New England Biolabs) and then either cloned blunt-ended or, if restriction sites were placed in the primers, cloned after digestion with the appropriate enzymes. Such fragments were subcloned into appropriately cut and phosphatased M13mp10 vector (Amersham). Oligonucleotides were radiolabeled by kinasing (T. Maniatis, E. F. Fritsch, J. Sambrook, *Molecular Cloning: A Laboratory Manual* (Cold Spring Harbor Laboratory, Cold Spring Harbor, N.Y., 1982)). Oligonucleotide hybridization conditions were 6X SSCP, 2X Denhardt's, 2mM EDTA, 0.05% sodium pyrophosphate, 0.1% SDS, 100 mcg/ml yeast tRNA as non-specific competitor, pH 8.0. The temperature of hybridization and the stringency conditions for washing hybridized blots and filters were adjusted individually for each oligonucleotide probe based on its relative GC content. Long, radiolabeled DNA probes were prepared by random priming [A. P. Feinberg and B. Vogelstein, *Anal. Biochem.* 132, 6 (1983)]. Hybridization conditions using such probes were: 5X SSCP, 2X Denhardt's, 2 mM EDTA, 0.05% sodium pyrophosphate, 0.1% SDS, 250 μg/ml herring sperm DNA, pH 8.0 at 65° C.; washing at 65° C. in 0.1X SSCP and 0.1% SDS. Sequencing was done by the dideoxy chain termination method [F. Sanger, S. Nicklen, A. R. Coulson, *Proc. Natl. Acad. Sci. U.S.A.* 74, 5463 (1977)] using as template single-stranded DNA prepared from subclones in both orientations in M13 vectors.

EXAMPLE 2

Production of Recombinant NGF in *E. Coli*

A synthetic gene encoding the mature (processed) form of human NGF was purchased from British Biotech. This gene is identical to the human nucleic acid sequence reported for NGF (Ullrich et al. 1983 ibid.), except for changes in the human nucleic acid sequence made to insert a variety of restriction sites and is supplied in the plasmid BBG26.

The plasmid was transformed into *E. coli* strain DH5alpha to produce the plasmid in sufficient quantity for subsequent operations. In order to modify this synthetic gene for insertion into an appropriate expression vector, the following two oligonucleotides were synthesized:

EcoRI site located near the 5' end of the synthetic NGF gene. After exposure of BBG26 to the restriction enzyme EcoRI, the synthetic oligonucleotide can be ligated to the cut plasmid just 5' of the EcoRI site, thus replacing the 5' portion of the NGF coding sequence. This replacement of the 5' end of the coding sequence allows the insertion of an upstream translational coupler (see above oligonucleotide sequences) and the substitution of codons preferred by *E coli*. (according to deBoer and Kastelein in *From Gene to Protein: Steps Dictating the Maximal Level of Gene Expression* (1986) Davis and Reznikoff, eds. pp. 225-283, Butterworths, N.Y.). These changes are designed to promote efficient expression of the NGF sequences.

The oligonucleotide NGF-A and NGF-B were kinased and annealed together then ligated to the EcoRI-cut and phosphatased plasmid BBG26 and the mixture phosphatased. The mixture was treated with the restriction enzyme BamHI and the approximately 390 bp BamHI fragment containing the modified NGF coding sequence was gel purified. This fragment was ligated to each of two different gel-purified, BamHI-cut, and phosphatased *E. coli* expression vectors: (1) a vector based on a T7 phage promoter system, called pT5T; or, (2) a vector based on a hybrid 'Tac' promoter derived from both the tryptophan and lactose, called pT3XI-2 (see Experimental Appendix to this Example and FIGS. 4 & 5 for details). This resulted in the formation of either pT5T:NGF or pT3XI-2:NGF.

pT5T:NGF was transformed into *E. coli* strain BL21(DE3). This strain (described in Studier and Moffat *J. Mol. Biol.* (1986) 189:113-130) contains the T7 RNA polymerase gene under control of the IPTG inducible lac promoter on a nonexcisable lysogenic lambda bacteriophage. Since the insert in the pT5T vector is under control of the T7 phage promoter, this ultimately places expression of the inserted sequences under control of the lac promoter, hence expression is inducible by isopropyl β-D-thiogalatopyranoside (IPTG). Transformants were picked, grown up, and hybridized with the $^{32}$P-labeled 390-bp BamHI fragment to determine which transformants carried the NGF insert. Eight positives were selected, grown up, and vector DNA was prepared and sequenced. Each of the eight carried the correct insert in the correct orientation. Two were grown up separately in Luria broth containing 15 mcg/ml tetracycline to an optical density (O.D.) of ca. 0.6, then the cultures were induced by addition of 1 mM final concentration of IPTG. Samples of each culture were taken at intervals from 2 to 21 hr after induction and lysed in SDS-PAGE sample buffer (0.025% bromphenol blue, 10% glycerol, 1% β-mercaptoethanol, 2% SDS, 0.0625M Tris-HCl, pH 6.8). Each sample was electrophoresed by reducing SDS-PAGE and production of NGF monitored both by the appearance of a Coomassie-brilliant-blue-stained band

```
NGF-A
             Translational
   BamHI     Coupler
5'-GATC  CGATCTTGGAGGATGATTAA ATG TCC TCC TCC CAC CCG ATC
TTT CAC CGC GGC G-3'

NGF-B
    EcoRI
5'-AAT TC GCC GCG GTG AAA GAT CGG GTG GGA GGA GGA CAT
TTAATCA TCCTCCAAGATCG-3'
```

These oligonucleotides contain a BamHI site at the 5' end and an EcoRI site at the 3' end. There is a unique at the correct molecular weight and by Western blot analysis using antibody to mouse submaxillary gland NGF (Sigma). As negative controls, samples were taken from identical cultures not induced and from cultures of bacteria transformed with the pT5T vector not containing the NGF insert. The results shown in FIG. 2 indicate that transformant pT5T:NGF-18 produces a protein band at the molecular weight expected for processed NGF that is also recognized by anti-NGF antiserum (lanes labeled: pT5T:NGF-18 2,4,6,8,10, and 21 hrs of induction with IPTG). As expected, this band is not detectable in bacteria transformed with pT5T without the NGF insert (lanes labeled: pT5T u (uninduced) and i (induced)) or in pT5T:NGF-18 not induced by the presence of IPTG (lane labeled: pT5T:NGF-18 0 hours of induction with IPTG).

pT3XI-2:NGF was transformed into a phage-resistant E. coli K-strain, JM107. Thirteen transformants were grown up as for pT5T:NGF transformants and 3 were found to express the human mature NGF protein by SDS-PAGE of cell extracts after both staining with Coomassie Brilliant Blue and immunostaining with anti-mouse NGF antiserum as above for pT5T:NGF transformants.

Amino-terminal amino acid sequence of the recombinant NGF produced by pT3XI-2:NGF in E. coli JM107 indicated that the amino-terminal methionine had been removed during expression in at least 85% of the NGF produced. This indicates that the NGF being produced has the correct amino-terminus for processed mature human NGF.

The NGF produced as described herein was found to have no detectable biological activity as determined by the procedures set forth in Example 3 below.

EXPERIMENTAL APPENDIX TO EXAMPLE 2

1. Description of pT5T, an Expression Vector Based on the "T7 Promoter" System (Please refer to FIG. 4 for features of the vector)

The T7 promoter based expression vector pT5T is essentially the same as pJU1003 [Squires, et. al., *J. Biol. Chem.* (1988) 263:16297–16302], except that there is a short stretch of DNA between the unique BglII site 5' to the T7 promoter and the ClaI site in the tetracycline resistance gene. The sequence of this DNA is:

```
ClaI
ATCGATGATA AGCTGTCAAA CATGAGAATT GAGCTCCCCG GAGATCCTTA
GCGAAAGCTA AGGATTTTTT TTAGATCT
                              BglII
```

2. Description of pT3XI-2: a Modification of pKK223-3 Using a Hybrid 'Tac' Promoter System (Please refer to FIG. 5 for features of the vector)

The starting plasmid for this construction was plasmid pKK223-3 purchased from Pharmacia. Plasmid pKK223-3 carries a partial gene for tetracycline resistance. This non-functional gene was replaced by a complete tetracycline resistance gene carried on plasmid pBR322. Plasmid pKK223-3 was digested completely with SphI and partially with BamHI. A 4.4 kilobase pair fragment was gel purified and combined with a synthetic adaptor with the sequence:

```
5' GATCTAGAATTGTCATGTTTGACAGCTTATCAT     3'
3'     ATCTTAACAGTACAAACTGTCGAATAGTAGC 5'
``` and a 539 base pair fragment of DNA from a Cla I, Sph I digest of the tetracycline resistance gene of pBR322 (PL Biochemicals, 27-4891-01). The resulting plasmid was designated pCJ1.

Next a XhoI linker purchased from New England Biolabs was inserted into plasmid pCJ1's PvuII site to form plasmid pCJX-1. This insertion disrupts the rop gene which controls plasmid copy number. An EcoRI fragment containing the lac 1 gene was purified from plasmid pMC9 [Calos, et al., *Proc. Natl. Acad. Sci. USA* (1983), 80:3015–3019] then inserted into the XhoI site with XhoI to EcoRI adapters having the sequence:

```
5' TCGAGTCTAGA     3'
3'     CAGATCTTTAA 5'
```

The polylinker sequence between the EcoRI and Pst I sites in plasmid pKK223-3 was next replaced with a polylinker sequence shown here:

```
5' AATTCCCGGG TACCAGATCT GAGCTCACTA GTCTGCA 3'
3'     GGGCCC ATGGTCTAGA CTCGAGTGAT CAG     5'
```

The plasmid vector so obtained is designated pCJXI-1.

Finally, the tetracycline resistance gene was replaced with a similar gene which had the recognition sites for restriction enzymes Hind III, Bam HI, and Sal I destroyed by bisulfite mutagenesis. The following procedure was used to mutate the tetracycline resistance gene of pBR322. Plasmid pBR322 was cut with Hind III, then mutagenized with sodium bisulfite [Shortle and Nathans, *Proc. Natl. Acad. Sci. USA* (1978) 5:2170–2174]. The mutagenized DNA was ligated to form circular DNA, then cut with Hind III to linearize any plasmid that escaped mutagenesis. E. coli JM109 [Yanisch-Perron, et al., *Gene* (1985) 33:103–119] was transformed with the plasmid, then plated on selective media. Plasmids were isolated from tetracycline resistance colonies and checked for loss of the Hind III site in the tetracycline resistance gene. The successfully mutated plasmid was designated pT1. A similar procedure was followed to mutagenize the Bam HI site in pT1, yielding plasmid pT2. Plasmid pT2 in turn was mutagenized to remove the Sal I site, forming plasmid pT3. A ClaI/BsmI fragment of pT3 carrying the mutated tetracycline resistance gene was isolated and used to replace the homologous fragment of pCJXI-1 to form pT3XI-2. The mutated tetracycline resistance gene still encodes a functional protein.

3. Formation of pT3XI-2-φ10TC3FGFsyn (Preparing the Tac Promoter Vector for NGF)

Initially a "gene" for basic Fibroblast Growth Factor (bFGF) was synthesized. This "gene" codes for the same sequence as that reported for FGF by Sommer et al.(1987 *Biochem. Biophys. Res. Commun.* 141:67) but uses the codons that are found preferably in highly expressed genes in *E. coli*. The structure of this gene is such that the coding portion is preceded by a translational coupler sequence (see Squires, et al., 1988, ibid.) to ensure efficient initiation of translation.

The FGF synthetic gene was first inserted into M13mp18 between the EcoRI and Hind III sites and sequenced. The structure of this gene is:

```
AATTCAGGA TCCGATCGTG GAGGATGATT AAATGGGTAC CATGGCTGCT GGCTCCATCA
        GTCCT AGGCTAGCAC CTCCTACTAA TTTACCCATG GTACCGACGA CCGAGGTAGT
EcoRI   BamHI       RBS                     FGFstart
                Translational Coupler 3

CTACCCTGCC GGCACTGCCG GAAGACGGTG GCTCCGGTGC TTTCCCGCCG GGCCACTTCA
GATGGGACGG CCGTGACGGC CTTCTGCCAC CGAGGCCACG AAAGGGCGGC CCGGTGAAGT

AAGACCCGAA ACGTCTGTAC TGTAAAAACG GTGGCTTCTT CCTGCGTATC CACCCGGATG
TTCTGGGCTT TGCAGACATG ACATTTTTGC CACCGAAGAA GGACGCATAG GTGGGCCTAC

GTCGTGTCGA CGGCGTACGT GAAAAAAGCG ACCCGCACA TCAAACTGCA GCTGCAGGCTG
CAGCACAGCT TGCCGCATGC ACTTTTTTCC TGGGCGTGT AGTTTGACGT CGACGTCCGAC

AAGAACGTG GTGTTGTATC TATCAAAGGC GTTTGCGCAA ACCGTTACCT GGCTATGAAAG
TTCTTGCAC CACAACATAG ATAGTTTCCG CAAACGCGTT TGGCAATGGA CCGATACTTTC

AAGACGGTC GTCTGCTGGC TAGCAAATGT GTAACTGACG AATGTTTCTT CTTCGAACGTC
TTCTGCCAG CAGACGACCG ATCGTTTACA CATTGACTGC TTACAAAGAA GAAGCTTGCAG

TGGAAAGCA ACAACTACAA CACCTACCGT TCTCGTAAAT ACACTTCTTG GTACGTTGCTC
ACCTTTCGT TGTTGATGTT GTGGATGGCA AGAGCATTTA TGTGAAGAAC CATGCAACGAG

TGAAACGTA CCGGCCAGTA CAAACTGGGT TCCAAAACTG GCCCGGGTCA GAAAGCAATCC
ACTTTGCAT GGCCGGTCAT GTTTGACCCA AGGTTTTGAC CGGGCCCAGT CTTTCGTTAGG

TGTTCCTGC CGATGAGCGC TAAATCTTAA ACTAGTA
ACAAGGACG GCTACTCGCG ATTTAGAATT TGATCATTCGA
                    FGFstop        HindIII
```

Relevant features of the gene are highlighted.

It was then isolated by digestion with Bam HI and Hind III and inserted into Bam HI/Hind III-cut pJU1003 (Squires, et al., 1988, ibid.) yielding pJU1003-synFGF. This plasmid was cut with Xba I and Hind III and the Xba I/Hind III fragment carrying the FGF gene was isolated. This fragment was ligated into pT3XI-2 cut with EcoRI and Hind III, using an EcoRI-XbaI linker:

```
5'  AAT TCC ACA ACG GTT TCC CT      3'
3'      GG TGT TGC CAA AGG GAG ATC  5'
```

The new plasmid is designated pT3XI-2-φ10TC3FGFsyn.

4. Inserting NGF Expression Construct into the Tac Promoter Vector pT3XI-2-φ10TC3FGFsyn was cut with BamHI, which resulted in the linearization of the 7.4-kb expression vector and the release of the ca. 0.5-kb FGF DNA fragment. The 390-bp BamHI fragment containing the modified NGF coding sequences was ligated into the gel purified Bam HI-cut vector DNA fragment, resulting in the plasmid pT3XI-2:NGF.

EXAMPLE 3

Refolding and Renaturation of Members of the NGF/BDNF Family of Neurotrophic Proteins A. The Refolding of Mature NGF Produced in Eukaryotic Cells or Purified from Natural Sources One embodiment of the present invention involves the ability to refold and restore biological activity to the inactive, mature form of recombinant NGF produced in bacteria. To demonstrate that this is possible, it was first established that fully biologically active, mature NGF, produced in a eukaryotic cell expression system or purified from natural sources, can be successfully refolded after its biological activity has been destroyed by denaturation and reduction of disulfide bonds. This demonstration is significant for two reasons:

(1) It is reasonable to propose that after being fully denatured and reduced, mature NGF produced in bacteria (originally inactive), or purified from natural sources (originally active), or purified from natural sources (originally active) will be inactive and structurally indistinguishable. Since they are indistinguishable structurally, successful refolding of denatured and reduced mature NGF from eukaryotic cells or natural sources indicates that mature NGF expressed from bacteria, after being denatured and reduced, can also be successfully refolded.

(2) The full-length NGF precursor cannot be proteolytically processed in bacteria to produce the correct mature NGF, as it is in eukaryotic cell expression system. Therefore, in bacteria it is necessary to express the coding sequence for mature NGF directly and not that for the full-length precursor. It is theoretically possible that the proper folding and assumption of biological activity of mature NGF will only occur if it is first synthesized as the full-length precursor, as occurs in eukaryotic cells and in natural sources. This would eliminate any likelihood of successfully refolding the mature protein produced in bacteria. However, successful refolding of denatured and reduced mature NGF, as demonstrated herein, proves that proper refolding does not depend on the full-length precursor.

Figure 3:
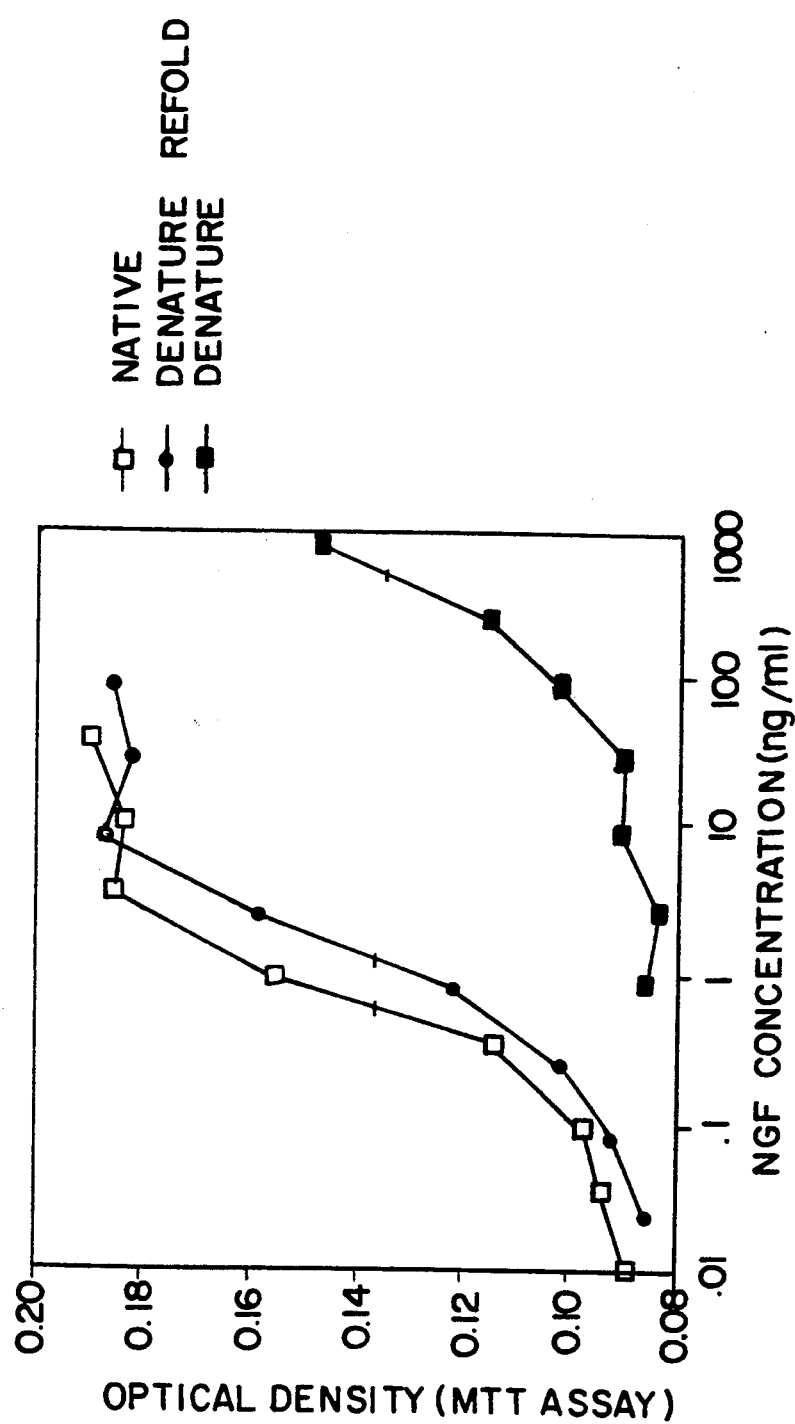
FIG. 3 depicts the loss and regaining of biological activity upon denaturation and refolding, respectively, of mature human NGF produced in eukaryotic cells.

Two forms of originally biologically active, mature NGF were successfully refolded after being denatured and reduced: (1) mature (beta) NGF purified from male mouse submaxillary gland (SIGMA), and (2) recombinant human mature NGF produced in eukaryotic cells according to procedures described in European Patent Publication EP 89113709. FIG. 3 demonstrates that the recombinant human mature NGF produced as above promotes the survival of chick embryo sympathetic ganglion neurons at the concentrations expected for NGF (Greene 1977 *Develop. Biol.* 58:96–113). FIG. 3 also demonstrates that this biological activity is lost after denaturation and reduction of disulfide bonds. FIG. 3 further demonstrates that full biological activity is restored to the denatured and reduced protein after it is refolded according to the procedures described herein. Essentially similar results were obtained using mature beta-NGF purified from mouse submaxillary gland. These successful refoldings indicate strongly the feasibility of refolding mature NGF produced in bacteria.

1. Protocol for Refolding NGF

NGF was dissolved at a concentration of 0.5 mg/ml in PBS (0.15M NaCl, 0.04M $K_2HPO_4$, 0.02M $KH_2PO_4$, pH7.2) and denatured by addition of guanidine hydrochloride to a final concentration of 3M. After 30 minutes at 25° C., dithiothreitol (DTT) was added to a final concentration of 5.6 mM and incubation was continued at 25° C. for another 2 hours (50 mM DTT has also been used with about equal success). Oxidized glutathione was then added to a final concentration of 50 mM and incubated at 25° C. for 10 minutes. This solution was diluted 7-fold in 0.6% Tris (Boehringer/Mannheim 604-205), not pH adjusted, containing 0.2% human serum albumin. L-cysteine was added to a final concentration of 20 or 30 mM with about equal success. This refolding mixture was incubated at 25° C. for 16–20 hours, then the material was concentrated with a Centricon-10 concentrator (Amicon) and the buffer exchanged with PBS.

2. Assay of NGF Biological Activity After Refolding

Untreated starting NGF, NGF left in the denaturing buffer containing 3M guanidine and 5.6 mM DTT, and denatured then refolded NGF were assayed for their ability to promote the survival of neurons from dissociated E11 chick embryo lumbar sympathetic chain ganglia, as described in the Experimental Appendix to this Example. FIG. 3 shows the results of this bioassay. The denatured and reduced NGF exhibited half-maximal biological activity at 450 ng/ml, whereas the starting NGF and the refolded NGF exhibited half-maximal biological activity at 0.5 and 1.0 ng/ml, respectively. These results indicate that denaturation and chemical reduction lowered the biological activity of recombinant human mature NGF by a factor of roughly 1,000 and that the refolding procedure restored to this material the biological activity found in the starting NGF within the roughly 2-fold experimental error of the bioassay.

B. The Refolding of Mature Human NGF Produced in *E. coli* Cells

Mature NGF expressed in *E. coli* cells as described in Example 2 above is biologically inactive. Such NGF is refolded to produce biologically active NGF according to the procedures described below.

1. Preparation of the Starting Material for Refolding 10 grams *E. coli* cell paste was resuspended in 50 ml of 10 mM EDTA, pH 7.0, and run through a French pressure cell twice at 16,000 psi. The cell extract was spun down at 16,000 xg for 20 minutes and the supernatant was discarded. The pellet was homogenized in 100 ml of 10 mM EDTA, pH 7.0. The resuspended pellet was centrifuged as above and the supernatant discarded. The pellet was again homogenized in 100 ml of 10 mM EDTA, pH 7.0. The resuspended pellet was centrifuged as above and the supernatant discarded. The pellet was homogenized with 30 ml of 4M urea in 50 mM Tris, pH 8.0, and 0.2% $\beta$-mercaptoethanol. The resuspended pellet was spun down and the supernatant discarded, as above. The pellet was homogenized with 30 ml of 20 mM sodium citrate, pH 3.0, containing 8M urea. The resuspended pellet was spun down as above and the supernatant place on ice. The pellet was homogenized in 30 ml of 20 mM sodium citrate, pH 3.0, containing 8M urea, centrifuged as above and the supernatant placed on ice. The supernatants can be stored at $-80°$ C.

2. Refolding of the *E. coli* Extract

To the final supernatant extract described above is added one-fourth volume of 1M Tris, pH 8.5, containing 8M urea. Dithiothreitol is added to a final concentration of 5–15 mM and the solution placed at 25° C. for 1 hour. Then cystine (or oxidized glutathione) is added to a final concentration of 15–50 mM and the solution placed at 25° C. for 10–15 minutes. Nine volumes of 100 mM $Na_2HPO_4$, pH 8.3, containing 3.2–4.2M urea is added followed by cysteine at 2–3 times the final concentration of cystine (or glutathione). The solution is held at 4° C. overnight. These conditions do not reduce or denature active NGF.

The preceding conditions provide ranges of concentrations and alternate reagents that we have found acceptable. The following provides an example of an actual refolding experiment:

Forty ml of the *E. coli* extract described above (containing approximately 650 $\mu$gm/ml of NGF as estimated by laser densitometry of coomassie brilliant blue-stained SDS-polyacrylamide gels) received 10 ml of 1M Tris, ph 8.5, containing 8M urea. Two ml of 400 mM dithiothreitol was added and the solution placed at 25° C. for 1 hour. Four ml of 600 mM oxidized glutathione was added and the solution placed at 25° C. for 15 minutes, at which time 450 ml of 100 mM $Na_2HPO_4$, pH 8.3, containing 3.2M urea was added, followed by 6 ml of 1M cysteine. The solution was placed at 4° C. for 16 hours. This solution is referred to below as the final refolding mixture.

3. Determination of the Efficiency of Refolding

The total amount of NGF in a final refolding mixture was determined as follows: Laser densitometry scans were performed after coomassie brilliant blue staining of SDS-polyacrylamide gels run under reducing conditions in which some lanes contained different concentrations of an NGF calibration standard (the baculovirus insect cell-produced material described in Example 3) while some lanes contained aliquots of the final refolding mixture. By establishing the quantitative relationship between the laser densitometry optical density and the amount of NGF standard protein, one can determine the amount of NGF in an unknown sample.

The amount of properly refolded NGF in a final refolding mixture was determined as follows: Serial dilutions of the final refolding mixture were tested for their ability to promote the survival of chick embryo sympathetic chain neurons in vitro in the assay described in the Experimental Appendix to Example 3. In the same assay, a range of concentrations of the standard insect cell-produced NGF were also tested for their ability to promote neuronal survival. The dilution of final refolding mixture that gave half-maximal survival in the bioassay was considered to contain the same concentration of properly refolded NGF as the concentration of standard NGF needed to give half-maximal survival.

These methods were used to determine the amount of properly refolded NGF in the experimental refolding described above. In the bioassay, 3.7 ng/ml of insect cell-produced NGF was required to give half-maximal survival. Since a dilution of 1:1500 of the final refolding mixture gave half-maximal survival, it was concluded that the final refolding mixture contained (1500×3.7=) 5550 ng/mL of active NGF. The total amount of NGF in the final refolding mixture was estimated by laser densitometry to be 52000 ng/ml, indicating a refolding efficiency of approximately 11%.

Figure 9:
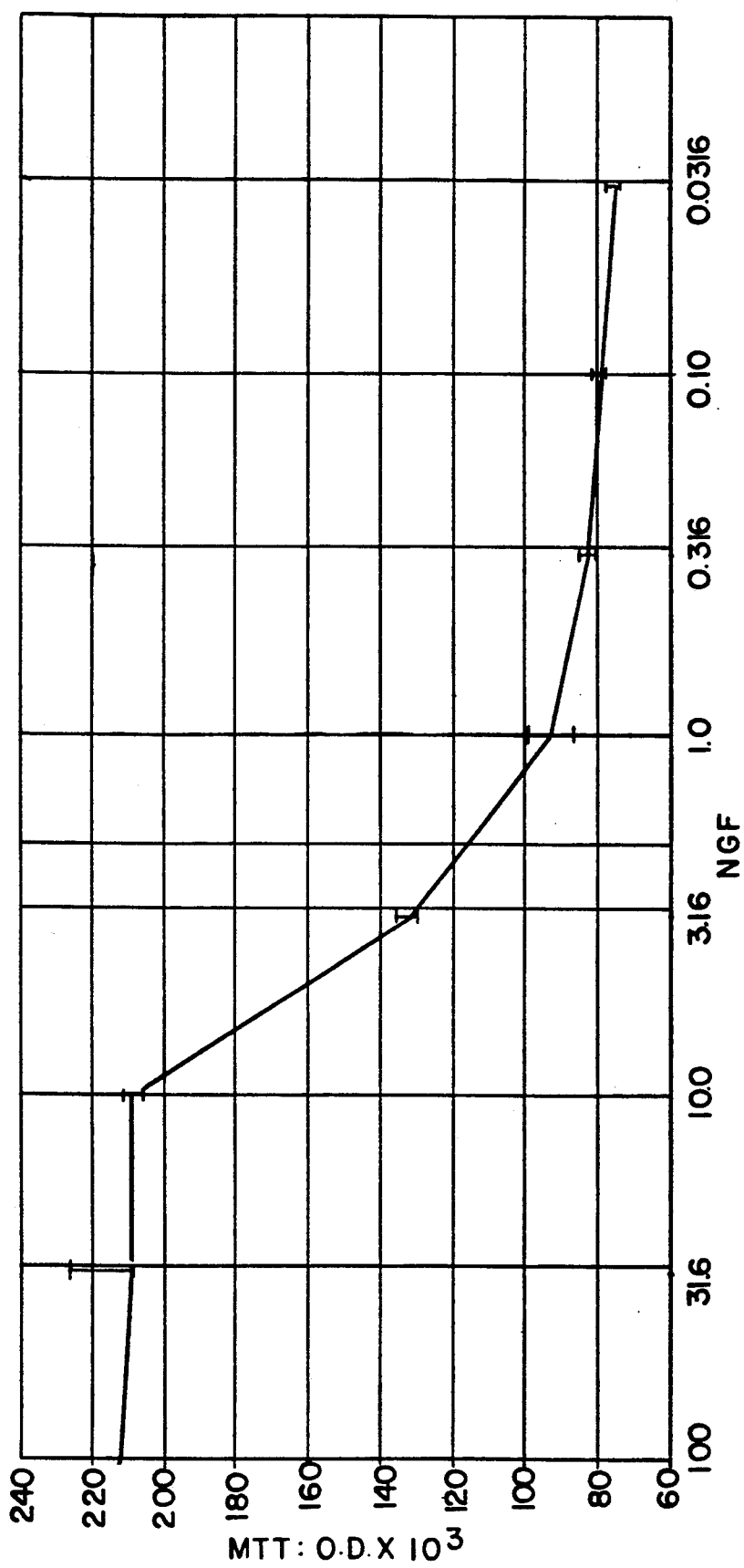
FIG. 9 depicts a dose-response curve for insect cell-produced human recombinant NGF using the bioassay on E11 chick embryo sympathetic ganglion neurons.
Figure 10:
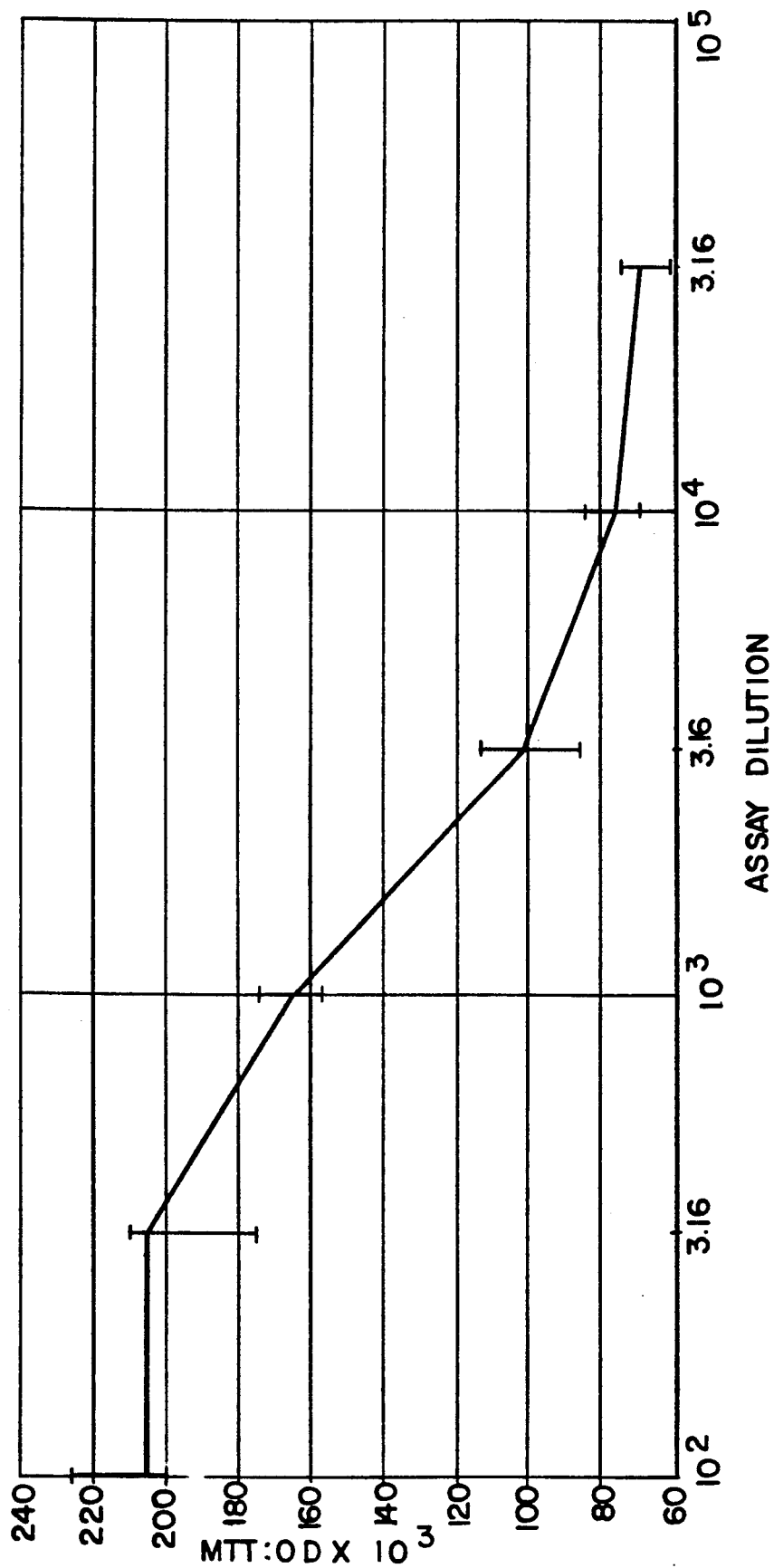
FIG. 10 depicts the bioactivity of serial dilutions of the final refolding mixture of *E. coli*-produced human recombinant NGF using the bioassay on E11 chick embryo sympathetic ganglion neurons.

FIG. 9 illustrates the bioassay results for the standard insect cell-produced NGF, which gave half-maximal survival at 3.7 ng/ml. FIG. 10 illustrates the bioassay results for the final refolding mixture, which gave half-maximal survival at a dilution of 1:1500.

4. Purification and Characterization of Refolded NGF Produced in *E. coli*

Reversed-phase high performance liquid chromatography (RP-HPLC) was used to purify and characterize the biologically active, refolded NGF in the final refolding mixture. The RP-HPLC conditions were as follows: solvent A=0.1% trifluoroacetic acid (TFA) in water; solvent B=0.1% TFA in acetonitrile (all HPLC grade reagents); column=VyDec C4 #214TP54; flow rate=1 ml per minute. The sample is injected at time 0 and the gradient developed with the following program:

| Time | % B |
| --- | --- |
| 0 | 5% |
| 5-10 | 5-20% |
| 10-40 | 20-50 |
| 40-50 | 50-80% |

The positions at which native NGF and reduced NGF were determined in order to calibrate the column for subsequent analysis of refolded samples. A sample of insect cell-produced, native NGF eluted at approximately 34% B. A sample of denatured and reduced insect cell-produced NGF eluted at approximately 43% B. The NGF was denatured and reduced by exposure to 6M guanidine hydrochloride and 50 mM dithiothreitol in 200 mM Tris, pH 8.5. Individual RP-HPLC columns required separate calibration with these standards to determine the exact % B at which these two samples eluted.

In 50 μl of the final refolding mixture from the experimental refolding described above, a peak of protein appeared at the position of native NGF (FIG. 11B). No protein ran at this position before refolding. When 100 ng of native insect cell-produced NGF was added to a second 50 μl sample, the size of the peak at the position of NGF approximately doubled (FIG. 11A). This confirmed that the protein that appeared after refolding ran at the same position as native NGF and also indicated that there was approximately 100 ng of this material in 50 μl of the final refolding mixture. Only this peak exhibited detectable bioactivity when fractions collected from across the RP-HPLC gradient were assayed for bioactivity in the sympathetic neuron survival assay. This further confirms the identity of this protein in the final refolding mixture as NGF. The specific activity of this peak was within the range of that observed for native insect cell-produced NGF (half-maximal survival at 0.5-5 ng/ml in separate assays on different days). Thus the refolded NGF from *E. coli* runs at the position of native insect cell-produced NGF and is fully biologically active.

C. The Refolding of Mature Human BDNF

Mature human BDNF, as described in Example 1 above, is made biologically active by refolding according to the procedures described in Example 3B. above.

D. The Refolding of Mature NGF-3

Mature human NGF-3, as described in Example 4 below, is made biologically active by refolding according to the procedures described in Example 3B. above.

EXPERIMENTAL APPENDIX TO EXAMPLE 3

1. Bioassay of NGF and BDNF

Cultures of chick embryo sympathetic chain and dorsal root ganglia were prepared as previously described (Collins and Lile 1989 *Brain Research* 502:99). Briefly, sympathetic or dorsal root ganglia were removed from fertile, pathogen-free chicken eggs that had been incubated for 8-11 days at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%. After this treatment, ganglia were transferred to a solution consisting of Dulbecco's high glucose Modified Eagle Medium without bicarbonate containing 10% fetal calf serum and 10 mM HEPES, pH 7.2 and mechanically dissociated by trituration approximately 10 times through a glass Pasteur pipet whose opening had been fire polished and constricted to a diameter such that it took 2 seconds to fill the pipet. The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50 μl per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water, and air dried.

10 μl of a serial dilution of the sample to be assayed for neurotrophic activity was added to each well and the dishes were incubated for 20 hours at 37° C. in a humidified atmosphere containing 7.5% $CO_2$. After 18 hours, 15 μl per well of a 1.5 mg/ml solution of the tetrazolium dye MTT in Dulbecco's high glucose modified Eagle Medium without bicarbonate containing 10 mM HEPES, pH 7.2 was added and the cultures placed back in the 37° C. incubator for 4 hours. Then, 75 μl of a solution of 6.7 ml of 12M HCl per liter of isopropanol was added and the contents of each well triturated 30 times to break open the cells and suspend the dye. The absorbance at 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The concentration of trophic activity in trophic units (TU) per ml was defined as the dilution that gave 50% of maximal survival of nerve cells. For example, if the sample gave 50% maximal survival when diluted 1:100,000 the titer was defined as 100,000 TU/ml. Specific activity was determined by dividing the number of trophic units per ml by the concentration of protein per ml in the undiluted sample.

EXAMPLE 4

Cloning NGF-3, A New Member of the NGF/BDNF Family of Neuroptrophic Proteins

A. Use of the Polymerase Chain Reaction (PCR) to Amplify a DNA Fragment of NGF-3

Two partially degenerate oligonucleotides, NNF-1 and NNF-3, were synthesized based on highly conserved regions of the nucleic acid sequences encoding the mature (processed) NGFs of various species and pig and human BDNF. The sequences of these oligonucleotides and 5' restriction sites inserted for ease of subcloning amplified fragments are presented below. (I=inosine)

NNF-1 (SENSE STRAND)

5'- GGAAGCTT GTG TG(C/T) GAC AG(C/T) (A/G)T(C/T) AG(C/T) (A/G) (A/T)G TGG GT -3'

NNF-3 (ANTI-SENSE STRAND)

BamHI
5'- CCGGATCC TTC CA(A/G) TG(C/T) (C/T)TI (A/G) (A/C) (A/G) TCI AT(G/C) CC(C/T) C(G/T)G CA-3'

Figure 7:
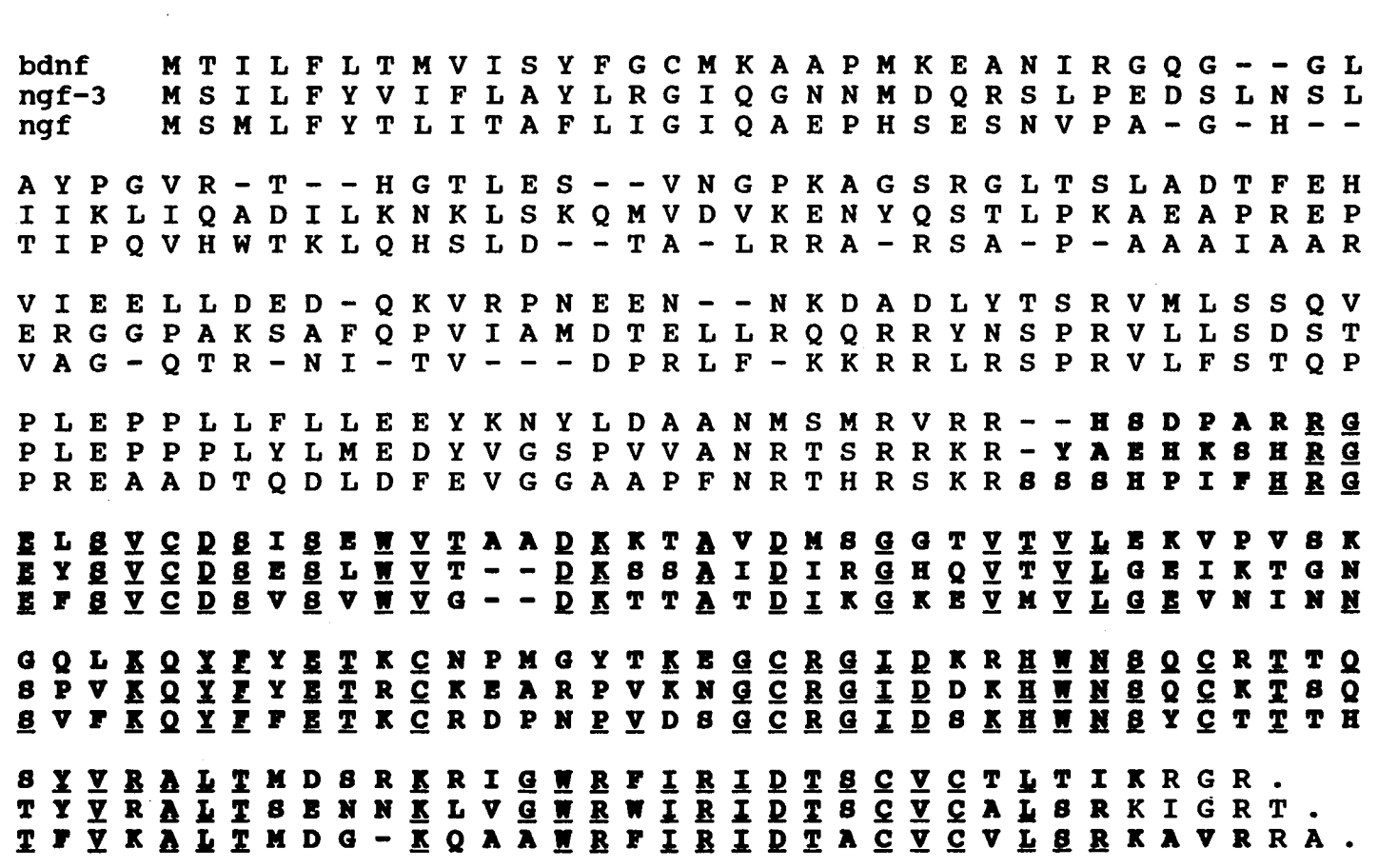

NNF-1 and NNF-3 were used as primers in PCR (see Experimental Appendix to Example 1) with human genomic DNA as template. The PCR products were electrophoresed in a 3% agarose gel and a fluorescent DNA band around the expected size of 150–200 bp was excised from the gel and cloned by blunt end ligation into SmaI-cut phage M13mp10. The resulting ligation reaction was plated on E. coli strain TG1 and duplicate lifts were taken. The first lift was hybridized at high stringency to the randomly-labeled human BDNF coding sequence obtained by PCR (see Example 1). The second lift was hybridized at high stringency to the randomly labeled human NGF mature protein coding sequence obtained from British Biotech (see Example 1). Any plaque that hybridized to either probe was not pursued further. All remaining plaques that contained an insert, as indicated by failure to produce beta-galactosidase, were sequenced. The phage in one such plaque, NNF-18, contained a 136-bp amplified DNA fragment between oligonucleotides NNF-1 and NNF-3 that coded for a protein fragment that is 53% identical to human NGF and 44% identical to human BDNF (FIG. 7). Some amino acid homologies are to both NGF and BDNF and some are unique to NGF or BDNF (FIG. 7). The NGF-3 fragment bears approximately the same homology to NGF or BDNF as the latter two proteins bear to each other (FIG. 7). The DNA sequence of this fragment is underlined in FIG. 6, where it is compared to NGF and BDNF. Based on these homologies, it was concluded that this fragment had been amplified from a gene for a new member of the NGF/BDNF family of neurotrophic proteins. The new gene and protein were named NGF-3.

B. Use of the DNA Amplified With PCR to Clone the Human Gene for NGF-3

The DNA fragment of NGF-3, amplified by PCR as above, was radiolabeled by performing PCR amplification in the presence of $^{32}P$-dCTP and used to screen a human genomic library in lambda FIX II (Stratagene cat. no. 946203). Six positives from $1.2 \times 10^6$ plaques were purified by repeated cloning. Partial digests of the DNA from one positive using the restriction enzyme HinCII were subcloned into M13. Several M13 subclones that hybridized to the radiolabeled PCR fragment were sequenced in both orientations according to the procedures described in Example 1B. above, in order to obtain the complete nucleic acid (FIG. 6) and inferred amino acid (FIG. 7) sequences for human NGF-3.

Expression of Mature Human NGF-3 in E. Coli

The human mature NGF-3 gene obtained as described in Example 4B. above, is inserted into E. coli expression vectors, such vectors are introduced into E. coli host cells, and expression of the gene to produce mature BDNF is accomplished according to the procedures described in Example 2 above by replacing the NGF-3 gene for the NGF gene.

The above description and examples set forth a description of the invention and the preferred embodiments thereof. Many modifications of the methods described herein will be obvious to those of ordinary skill in the art and are within the scope of the claims as set forth below.

We claim:

1. A method for folding human mature nerve growth factor (NGF), recombinantly expressed in E. coli, wherein the protein attains substantially full biological activity which comprises:

dissolving said *E. coli* expressed NGF to a concentration of about 0.6 mg/ml in 20 mM sodium citrate, pH at about 3,0, containing 8 molar urea;

raising the pH of the dissolved solution by addition of a 1M Tris Solution, pH at about 8.5, containing 8M urea;

reducing said NGF by addition of dithiothreitol to a concentration of about 5-15 mM;

oxidizing said NGF by addition of oxidized glutathione or cystine to a concentration of about 15-50 mM;

diluting said solution of NGF about nine fold with a solution of 100 mM $Na_2HPO_4$, pH at about 8.0, containing about 3.2 to 4.2M urea;

catalyzing disulfide interchange of said NGF by addition of about 2 to 3 fold cysteine relative to the concentration of glutathionine of cystine; and isolating said NGF from said reaction mixture.

2. A method for refolding and renaturing neurotrophic proteins recombinantly expressed in *E. coli*, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3);

said method comprising:

disrupting all intramolecular and intermolecular disulfide bonds in a solution containing said neurotrophic protein to form free thiols by adding a denaturant and a reducing agent to said solution;

oxidizing said free thiols with a disulfide containing compound to form mixed disulfide bonds;

diluting said solution in the presence of a thiol containing compound; and isolating said neurotrophic protein from said solution.

3. The method of claim 2 wherein said disrupting comprises the steps of:

dissolving said *E. coli* expressed neurotrophic protein to a concentration of about 0.6 mg/ml in 20 mM sodium citrate, pH at 3.0, containing 8 molar urea;

raising the pH of said solution by addition of a 1M Tris solution, pH at 8.5, containing 8 molar urea; and reducing said NGF by addition of dithiothreitol to a concentration of about 5-15 mM.

4. The method of claim 2 wherein said disulfide containing compound is oxidized glutathione or cystine.

5. The method of claim 2 wherein said denaturant is guanidine hydrochloride or urea.

6. The method of claim 2 wherein said thiol containing compound is cysteine or dithiothreitol.

7. A method for refolding and renaturing neurotrophic proteins recombinantly expressed in *E. coli*, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3);

said method comprising:

dissolving said *E. coli* expressed neurotrophic protein to a concentration of about 0.6 mg/ml in 20 mM sodium citrate, pH at 3.0, containing 8 molar urea;

raising the pH of said solution by addition of a 1M Tris solution, pH at 8.5, containing 8 molar urea;

reducing said neurotrophic protein by addition of dithiothreitol to a concentration of about 5-15 mM;

oxidizing said neurotrophic protein by addition of oxidized glutathione or cystine to a concentration of about 15-50 mM;

diluting the solution of oxidized neurotrophic protein about nine fold with a solution of 100 mM $Na_2HPO_4$, pH at about 8,0, containing about 3.2 to 4.2M urea;

catalyzing disulfide interchange of said neurotrophic protein by addition of about 2 to 3 fold cysteine relative to the concentration of glutathione or cystine; and isolating said neurotrophic protein from the catalyzed reaction mixture.

* * * * *